(12) United States Patent
Kimura

(10) Patent No.: US 11,156,751 B2
(45) Date of Patent: Oct. 26, 2021

(54) IMAGING OPTICAL SYSTEM, CAMERA MODULE, AND ELECTRONIC DEVICE

(71) Applicant: SONY SEMICONDUCTOR SOLUTIONS CORPORATION, Kanagawa (JP)

(72) Inventor: Katsuji Kimura, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 100 days.

(21) Appl. No.: 16/340,846

(22) PCT Filed: Nov. 8, 2017

(86) PCT No.: PCT/JP2017/040287
§ 371 (c)(1),
(2) Date: Apr. 10, 2019

(87) PCT Pub. No.: WO2018/100992
PCT Pub. Date: Jun. 7, 2018

(65) Prior Publication Data
US 2019/0271800 A1    Sep. 5, 2019

(30) Foreign Application Priority Data

Nov. 29, 2016    (JP) .............................. JP2016-230962

(51) Int. Cl.
*G02B 5/20* (2006.01)
*H04N 5/225* (2006.01)
(Continued)

(52) U.S. Cl.
CPC ............... *G02B 5/205* (2013.01); *G02B 5/00* (2013.01); *G02B 5/208* (2013.01); *G02B 9/02* (2013.01);
(Continued)

(58) Field of Classification Search
USPC ........................................ 359/722, 723, 888
See application file for complete search history.

(56) References Cited

U.S. PATENT DOCUMENTS 3,700,314 A * 10/1972 Busby, Jr. .............. G02B 5/205
                                                        359/888
4,030,817 A *  6/1977 Westell .................. G02B 27/58
                                                        359/888
(Continued)

FOREIGN PATENT DOCUMENTS

| CN | 201725050 U | 1/2011 |
| JP | 08-292480 A | 11/1996 |
| JP | 10-022487 A | 1/1998 |

(Continued)

OTHER PUBLICATIONS

International Search Report and Written Opinion of PCT Application No. PCT/JP2017/040287, dated Jan. 23, 2018, 08 pages of ISRWO.

(Continued)

*Primary Examiner* — Darryl J Collins
(74) *Attorney, Agent, or Firm* — Chip Law Group

(57) ABSTRACT

An imaging optical system according to the present disclosure includes: a lens; and an optical member, in which the optical member is configured such that a light transmittance value at least in a peripheral portion is larger than a light transmittance value in a central portion. Furthermore, a camera module according to the present disclosure includes the imaging optical system of the present disclosure. Furthermore, an electronic device according to the present disclosure includes a solid-state imaging element and the imaging optical system of the present disclosure.

6 Claims, 13 Drawing Sheets

(51) Int. Cl.
*H04N 5/372* (2011.01)
*G02B 9/04* (2006.01)
*G02B 5/00* (2006.01)
*G02B 9/02* (2006.01)

(52) U.S. Cl.
CPC ............... *G02B 9/04* (2013.01); *H04N 5/225* (2013.01); *H04N 5/2254* (2013.01); *H04N 5/372* (2013.01)

(56) References Cited

U.S. PATENT DOCUMENTS

2004/0109240 A1* 6/2004 Sato ..................... G02B 7/102 359/704
2006/0158546 A1* 7/2006 Hirai .................... H04N 5/2254 348/335
2008/0239516 A1* 10/2008 Nakagawa ............... G02B 9/34 359/773
2014/0347493 A1* 11/2014 Higashitsutsumi .... G02B 5/208 348/164

FOREIGN PATENT DOCUMENTS

| | | |
|---|---|---|
| JP | 10-22487 A | 1/1998 |
| JP | 2007-292828 A | 11/2007 |
| JP | 2012-134771 A | 7/2012 |
| JP | 2013-152369 A | 8/2013 |
| JP | 2014-238527 A | 12/2014 |
| JP | 2015-079128 A | 4/2015 |

OTHER PUBLICATIONS

Office Action for CN Patent Application No. 201780072136.5, dated Jan. 15, 2021, 08 pages of Office Action and 09 pages of English Translation.

* cited by examiner

IMAGING OPTICAL SYSTEM, CAMERA MODULE, AND ELECTRONIC DEVICE

CROSS REFERENCE TO RELATED APPLICATIONS

This application is a U.S. National Phase of International Patent Application No. PCT/JP2017/040287 filed on Nov. 8, 2017, which claims priority benefit of Japanese Patent Application No. JP 2016-230962 filed in the Japan Patent Office on Nov. 29, 2016. Each of the above-referenced applications is hereby incorporated herein by reference in its entirety.

TECHNICAL FIELD

The present disclosure relates to an imaging optical system, a camera module, and an electronic device.

BACKGROUND ART

Recently, in imaging apparatuses such as a digital still camera and a mobile terminal apparatus with a camera, there is a trend of using a highly miniaturized camera with higher pixel resolution (with larger number of pixels). Furthermore, with this trend of using highly miniaturized cameras with higher pixel resolution, pixel pitch is becoming extremely small in a solid-state imaging element such as a CCD image sensor or a CMOS image sensor mounted on an imaging apparatus.

Under such circumstances, there is a problem of small aperture diffraction in a lens of an imaging optical system that captures image light (incident light) from a subject and guides the light to an imaging surface of a solid-state imaging element. In order to solve this problem of small aperture diffraction, it is necessary to increase the aperture of the lens. However, it is known that increasing aperture of the lens would induce another problem of reduction in the peripheral light amount (vignetting), that is, the amount of light decreases at peripheral portions (edge portions) of the screen, caused by optical characteristics of the lens.

Furthermore, the problem of reduction in the peripheral light amount has been generally handled with amplification of a signal at the peripheral portion of the screen where the amount of light has decreased, by using a signal processing system of the solid-state imaging element. However, the amplification processing in the signal processing system of the solid-state imaging element has problems of emphasized noise component, emphasized flaw in the solid-state imaging element, emphasized fine dust attached to the solid-state imaging element, emphasized unevenness of the solid-state imaging element or optical materials and the like, and these problems lead to reduction in the yield of the imaging apparatus.

Meanwhile, in order to solve the problem of small aperture diffraction, there is a proposed technology in which two gradation Neutral Density (ND) filters having continuously varying light transmittance are arranged to face each other, and symmetrically inserted/detached in the optical path for achieving a light amount adjustment apparatus having a wide variable density range (refer to Patent Document 1, for example).

Furthermore, there is another proposed technology that, in order to alleviate a decrease in the peripheral light amount, which might be caused by inserting an ND filter into the optical path at the time of execution of a camera shake correction function, changes the attenuation amount of light caused by the ND filter in accordance with a change in brightness and reduces an image blur correction range with the increase in the attenuation amount of light (refer to Patent Document 2, for example).

CITATION LIST

Patent Document

Patent Document 1: Japanese Patent Application Laid-Open No. 2007-292828
Patent Document 2: Japanese Patent Application Laid-Open No. 2012-134771

SUMMARY OF THE INVENTION

Problems to be Solved by the Invention

Although the known technology described in Patent Document 1 can solve the problem of small aperture diffraction, it does not take into consideration the problem of reduction in peripheral light amount due to the optical characteristics of the lens. In addition, although the known technology described in Patent Document 2 can suppress an unbalanced state of the peripheral light amount due to the effect of the ND filter, the problem of reduction in peripheral light amount due to the optical characteristics of the lens has not been taken into consideration, even with execution of the camera shake correction.

The present disclosure aims to provide an imaging optical system capable of optically correcting a decrease in the peripheral light amount caused by the optical characteristics of a lens, rather than by correction in signal processing, a camera module including the imaging optical system, and an electronic device using the camera module.

Solutions to Problems

An imaging optical system according to the present disclosure for achieving the above aims includes:
a lens; and an optical member,
in which the optical member is configured such that a light transmittance value at least in a peripheral portion is larger than a light transmittance value in a central portion.

Furthermore, a camera module according to the present disclosure in order to achieve the above described aim includes the imaging optical system according to the present disclosure.

Furthermore, an electronic device according to the present disclosure in order to achieve the above described aim includes a solid-state imaging element and the imaging optical system according to the present disclosure.

Effects of the Invention

In the imaging optical system, the camera module, or the electronic device according to the present disclosure, the light transmittance value at least in a peripheral portion of the optical member is larger than the light transmittance value in the central portion. Accordingly, nonuniformity of the light amount due to the decrease in light amount at the peripheral portion (edge portion) of the screen is optically corrected by the optical member. That is, according to the present disclosure, it is possible to optically correct the nonuniformity of the light amount due to the decrease in the peripheral light amount based on the optical characteristics of the lens by using the imaging optical system, rather than by correction in signal processing. Note that effects described herein are non-limiting. The effects may be any effects described in the present description. In addition, effects described herein are provided for purposes of exemplary illustration and are not intended to be limiting. Still other additional effects may also be contemplated.

MODE FOR CARRYING OUT THE INVENTION

Figure 1:
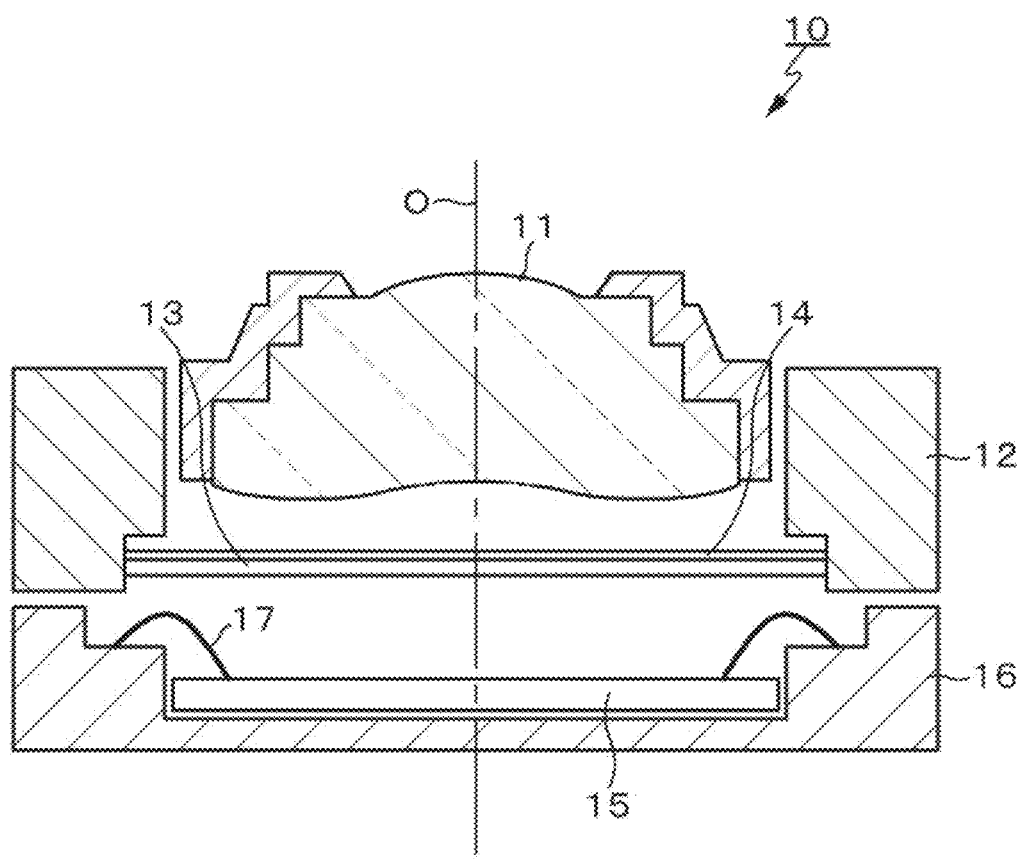
FIG. 1 is a cross-sectional view illustrating a cross-sectional structure of a camera module according to a first embodiment of the present disclosure.

Hereinafter, embodiments of the technology according to the present disclosure (hereinafter, embodiment(s)) will be described in detail with reference to the drawings. The technology according to the present disclosure is not limited to the embodiments. In the following description, the same elements or elements having the same function will be denoted by the same reference symbols, and duplicated description will be omitted. Note that description will be presented in the following order.

1. General description of imaging optical system, camera module, and electronic device according to the present disclosure 2. First embodiment (example of mounting solid-state imaging element on circuit substrate)

3. Second embodiment (example of accommodating a solid-state imaging element in package)

4. Electronic device according to the present disclosure (example of imaging apparatus)

5. Application example 5-1. Endoscopic surgery system 5-2. Device mounted on moving body 6. Constitution applicable by the present disclosure <General Description of Imaging Optical System, Camera Module, and Electronic Device of the Present Disclosure>

The camera module according to the present disclosure can have a configuration including a solid-state imaging element accommodated in a package including a light-transmissive material and configured to receive light that has passed through an imaging optical system. Here, the imaging optical system is naturally arranged on the light incident side of the solid-state imaging element.

In the imaging optical system according to the present disclosure, in the imaging optical system of the camera module according to the present disclosure including the above-described preferred configuration, and in the imaging optical system in the electronic device according to the present disclosure (hereinafter, these are collectively referred to as "imaging optical system or the like according to the present disclosure"), the optical member can be constituted by an ND filter in which light transmittance increases from a central portion toward a peripheral portion. Here, it is preferable that the ND filter has a gradation characteristic.

In the imaging optical system or the like of the present disclosure including the preferable configuration described above, the light transmittance of the optical member can be adapted to the light amount characteristic of the lens.

In the imaging optical system or the like according to the present disclosure including the various preferable configurations described above, the optical member can be disposed to be separated from the lens or can be formed on the lens. Specifically, in the former case, the optical member may be disposed to be separated from the lens on the light incident side of the lens, or may be disposed to be separated from the lens on the light emitting side of the lens. Furthermore, in the latter case, the optical member may be provided on the light incident surface of the lens, or may be provided on the light emitting surface of the lens, or both on the light incident surface and on the light emitting surface of the lens. In a case where the lens is constituted by a lens system having a combination of a plurality of lenses, the optical member is formed on at least one lens constituting the lens system.

The imaging optical system or the like of the present disclosure including the various preferable configurations described above can have a configuration
including an infrared cut filter and
in which the optical member is disposed to be separated from the infrared cut filter or is formed on the infrared cut filter.

Specifically, the optical member can be disposed separately from the infrared cut filter on the light incident side of the infrared cut filter, or can be provided on the light emitting side of the infrared cut filter so as to be separated from the infrared cut filter, or both on the light incident side and the light emitting side of the infrared cut filter so as to be separated from the infrared cut filter. Alternatively, the optical member may be formed on the light incident surface of the infrared cut filter, or may be formed on the light emitting surface of the infrared cut filter, or may be formed both on the light incident surface and the light emitting surface of the infrared cut filter. Furthermore, it is also possible to combine the optical member disposed to be separated from the infrared cut filter and the optical member formed on the infrared cut filter.

First Embodiment

The first embodiment of the present disclosure is an example of mounting a solid-state imaging element on a circuit substrate. FIG. 1 illustrates a cross-sectional structure of a camera module according to the first embodiment. The camera module according to the first embodiment includes an imaging optical system according to the present disclosure.

As illustrated in FIG. 1, the imaging optical system according to the first embodiment includes a lens (condenser lens 11) and an optical member (specifically, an ND filter 14), and the camera module 10 includes this imaging optical system. Specifically, the camera module 10 according to the first embodiment includes a condenser lens 11, a lens driving unit 12, an infrared cut filter (hereinafter referred to as "IR cut filter") 13, and the ND filter 14. The camera module 10 further includes a solid-state imaging element 15, a circuit substrate 16, and a metal wire 17.

In the camera module 10 having the above-described configuration, the condenser lens 11 captures and collects image light from a subject (not illustrated) as incident light, guides the light onto an imaging surface of the solid-state imaging element 15 through the IR cut filter 13 or the like. The lens driving unit 12 is formed with an actuator or the like, moves the condenser lens 11 in the direction of its optical axis O and stabilizes the condenser lens 11 at its optimum condensing position. The IR cut filter 13 is provided in an optical path of the imaging optical system, and removes infrared components contained in the image light collected by the condenser lens 11.

The optical member is configured such that a light transmittance value at least in a peripheral portion is larger than a light transmittance value in a central portion (peripheral portion of the optical axis O, including the optical axis O). That is, the optical member is formed with the ND filter 14 in which the light transmittance increases from its central portion to its peripheral portion. Here, the ND filter 14 has a gradation characteristic, for example. Note that an ND filter having a gradation characteristic is typically referred to as a gradation ND filter. In addition, the optical member (ND filter 14) is specifically formed on the infrared cut filter 13. More specifically, the ND filter 14 is formed with a filter membrane formed (deposited) over an entire surface of the surface (light incident surface) on the condenser lens 11 side of the IR cut filter 13. Here, the ND filter 14 is constituted by an absorptive ND filter, for example.

The gradation characteristic of the ND filter 14 is a characteristic that the value of the light transmittance increases from the optical center O (optical axis O) toward the peripheral portion (in other words, together with separation from the optical axis O). At this time, it is preferable that the light transmittance value continuously changes from the optical center O (optical axis O) toward the peripheral portion. Here, the term "continuous" includes a case where it is substantially continuous in addition to a case where it is strictly continuous, and allows various types of variations present due to design or the manufacturing process. Alternatively, the light transmittance value may change stepwise. The light transmittance of the optical member (ND filter 14) is adapted to the light amount characteristic of the condenser lens 11. That is, it is preferable that the light transmittance of the gradation characteristic of the ND filter 14 changes in accordance with the light amount characteristic of the condenser lens 11 provided in the optical path of the imaging optical system. That is, the gradation characteristic of the ND filter 14 is preferably set to allow the light transmittance value to change in accordance with the light amount characteristic of the condenser lens 11, that is, the light transmittance value preferably increases from the optical center O toward the peripheral portion.

The solid-state imaging element 15 is formed with a CCD image sensor, a CMOS image sensor, or the like. The solid-state imaging element 15 photoelectrically converts, on a pixel basis, the image light from the subject transmitted through the ND filter 14 and from which the infrared component has been removed by the IR cut filter 13. The circuit substrate 16 is formed by using a substrate material such as ceramic or glass epoxy. The solid-state imaging element 15 is mounted on the circuit substrate 16. The solid-state imaging element 15 is electrically connected to the circuit substrate 16 via the metal wire 17, for example. Peripheral circuits of the solid-state imaging element 15 or the like are formed on the circuit substrate 16.

As described above, the imaging optical system of the camera module 10 according to the first embodiment preferably has a configuration in which the ND filter (gradation ND filter) having a gradation characteristic that the value of the light transmittance increases from the optical center O toward the peripheral portion (in other words, together with separation from the optical axis O) is provided in the optical path of the imaging optical system.

Figure 2:
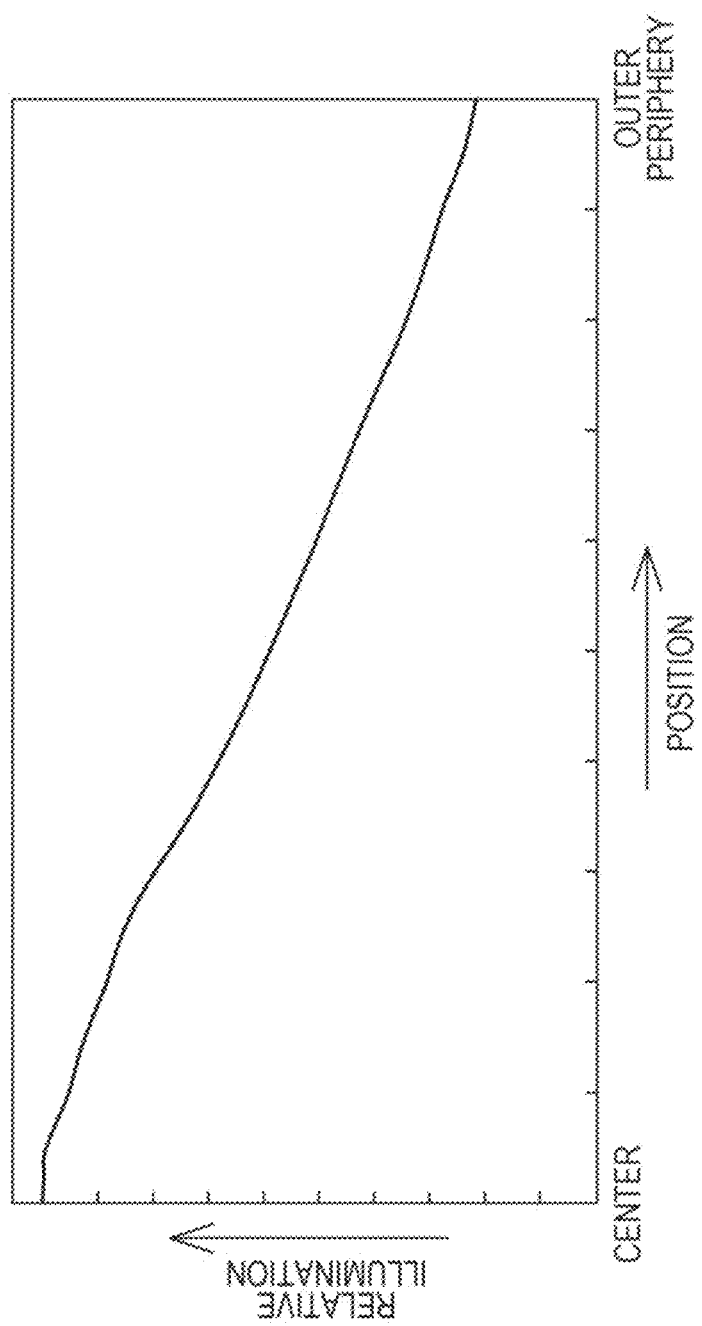
FIG. 2 is a characteristic diagram illustrating a peripheral light amount characteristic of a condenser lens.
Figure 3:
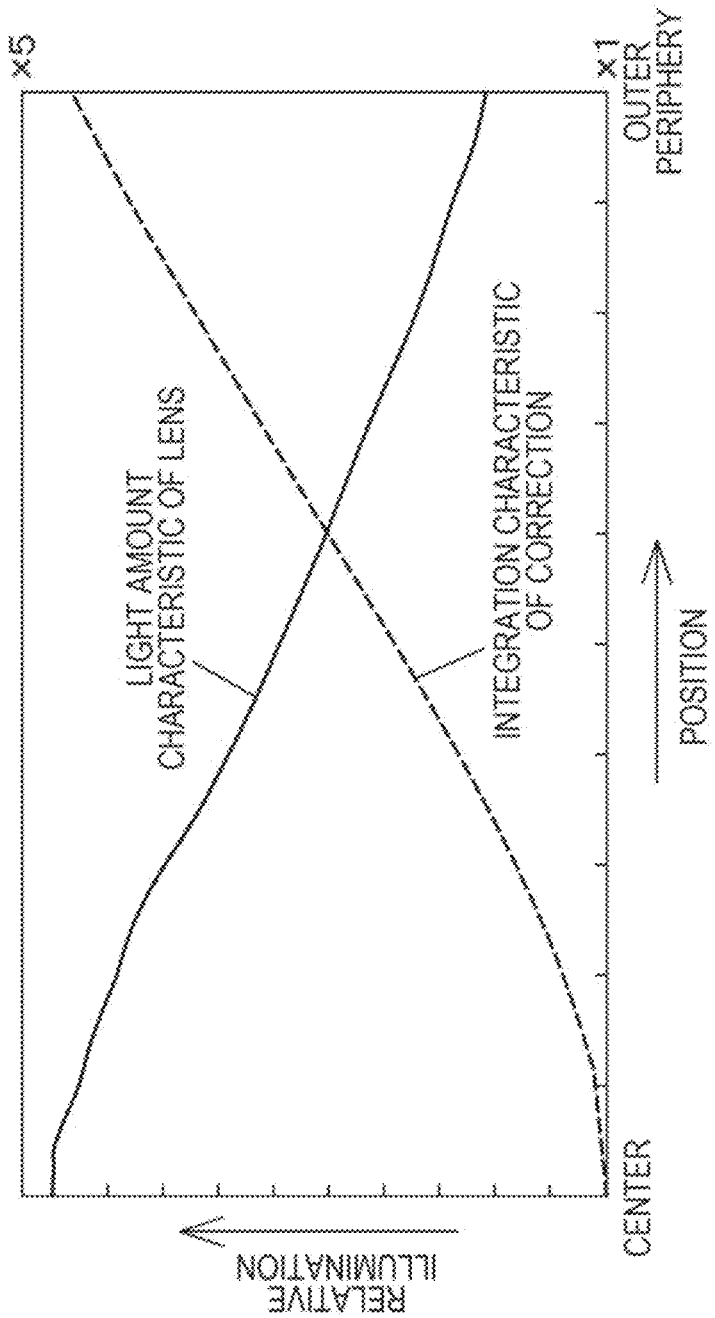
FIG. 3 is a characteristic diagram illustrating an integration characteristic of correction with respect to light amount characteristics of a condenser lens in a case where a decrease in peripheral light amount is corrected by a signal processing system.

Here, an imaging optical system without the gradation ND filter 14 will be discussed. As illustrated in FIG. 2, the peripheral light amount characteristic of the typical condenser lens 11 disposed in the optical path of the imaging optical system is represented by the light amount ratio of the peripheral portion being 20% with respect to the central portion. The problem of reduction in the peripheral light amount has been traditionally handled with correction of a signal at the peripheral portion of the screen where the amount of light has decreased, by using a signal processing system of the solid-state imaging element. FIG. 3 illustrates an integration characteristic of correction with respect to light amount characteristics of a condenser lens 11 in a case where the decrease in peripheral light amount is corrected by a signal processing system.

In a case where the decrease in the peripheral light amount is to be corrected by the signal processing system, the signal at the peripheral portion of the screen where the light amount has decreased is to be amplified. In this, however, the noise component is also amplified as well as the light amount component. As a result, the correction processing in the signal processing system would produce problems of emphasized noise component, emphasized flaw in the solid-state imaging element, emphasized fine dust attached to the solid-state imaging element, emphasized unevenness of the solid-state imaging element or optical materials, and the like, which might lead to reduction in the yield, additionally.

In contrast, the imaging optical system of the camera module 10 according to the first embodiment includes, in the optical path of the imaging optical system, the ND filter 14 in which the light transmittance value at least in a peripheral portion is larger than the light transmittance value in the central portion, which will lead to the following actions and effects. That is, in order to solve the problem of the small aperture diffraction of the condenser lens 11, the nonuniformity of the light amount caused by the reduction in the peripheral light amount caused by increasing the aperture of the lens can be optically corrected by the imaging optical system, rather than by correction using the signal processing that would cause problems such as emphasized noise component, emphasized flaw in the solid-state imaging element, and emphasized fine dust.

However, the present technology would not disclaim the correction in the signal processing, and it is also possible to adopt a mode that includes the optical correction in the imaging optical system as primary correction while including the correction in the signal processing as secondary correction. In other words, it is also possible to adopt a mode of using correction in signal processing to compensate for the correction in a region of the solid-state imaging element not sufficiently achieved by optical correction in the imaging optical system.

In other words, with a capability of optically correcting the reduction in the peripheral light amount, nonuniformity in the light amount due to the decrease in light amount would not occur even with a larger aperture of the condenser lens 11, leading to solution of the small aperture diffraction problem of the condenser lens 11. Moreover, capability of solving the problem of small aperture diffraction of the condenser lens 11 makes it possible to achieve miniaturization of pixels of a solid-state imaging element such as a CCD image sensor or a CMOS image sensor, leading to achievement of imaging of high-definition images.

In particular, the ND filter 14 has a gradation characteristic such that the light transmittance increases together with the light amount characteristic of the condenser lens 11 from the optical center O toward the peripheral portion, making it possible to achieve uniform brightness (luminance) over the region from the optical center O toward the peripheral portion. As a result, the optical design of peripheral brightness correction (shading correction) can be relaxed in the design of the condenser lens 11, making it possible to reduce the number of lenses constituting the condenser lens 11 Moreover, reduction in the number of lenses would lead to cost reduction and height reduction. In addition, the optical design for shading correction can be relaxed, making it possible to improve the distortion (image distortion).

Figure 4A:
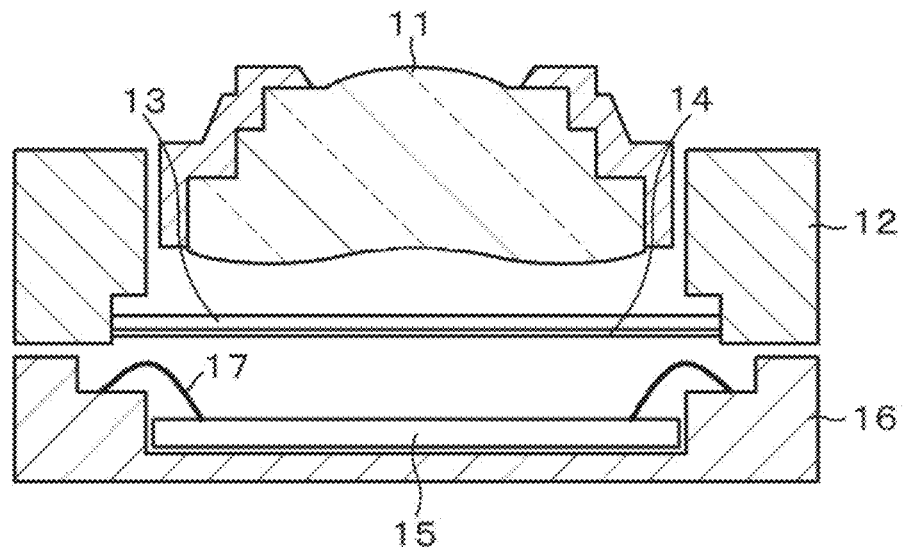
FIG. 4A is a cross-sectional view illustrating an example of a formation site of a gradation ND filter with respect to an infrared cut filter.

Note that while the first embodiment is an example where the ND filter 14 is formed (deposited) on the light incident surface of the IR cut filter 13, it would be also allowable to configure, as illustrated in FIG. 4A, such that the ND filter 14 is formed (deposited) on the light emitting surface (surface on the solid-state imaging element 15 side) or may be formed (deposited) on both the light incident surface and the light emitting surface. That is, as an optical member in which the light transmittance value at least in a peripheral portion is larger than the light transmittance value in the central portion, it is possible to have a configuration including the ND filter 14 formed on at least one of the light incident surface or the light emitting surface of the IR cut filter 13.

Figure 4B:
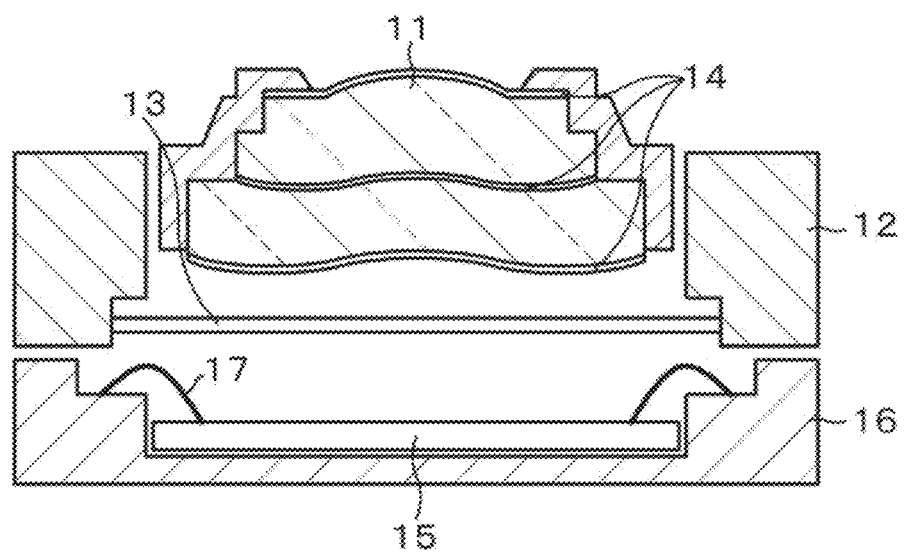
FIG. 4B is a cross-sectional view illustrating an example of a formation site of a gradation ND filter with respect to a condenser lens.

Furthermore, the optical member may be disposed to be separated from the condenser lens 11, or may be formed on the condenser lens 11. That is, as illustrated in FIG. 4B, the ND filter 14 may be formed (deposited) on at least one of the light incident surface or the light emitting surface of the condenser lens 11. Alternatively, as is well known, since the condenser lens 11 is formed with a combination of a plurality of lenses, the ND filter 14 may be formed (deposited) inside the condenser lens 11, specifically on a surface of the lens on the inner side of the condenser lens 11. That is, as an optical member in which the light transmittance value at least in a peripheral portion is larger than the light transmittance value in the central portion, it is possible to have a configuration including the ND filter 14 formed on at least one location out of the light incident surface of the condenser lens 11, inside of the condenser lens 11, and the light emitting surface of the condenser lens 11.

Note that the formation position of the ND filter 14 can be appropriately changed in accordance with the characteristics, processing accuracy, and the manufacturing method of the condenser lens 11, in any of the cases where the ND filter 14 is formed on the IR cut filter 13 side and formed on the condenser lens 11 side.

Figure 5A:
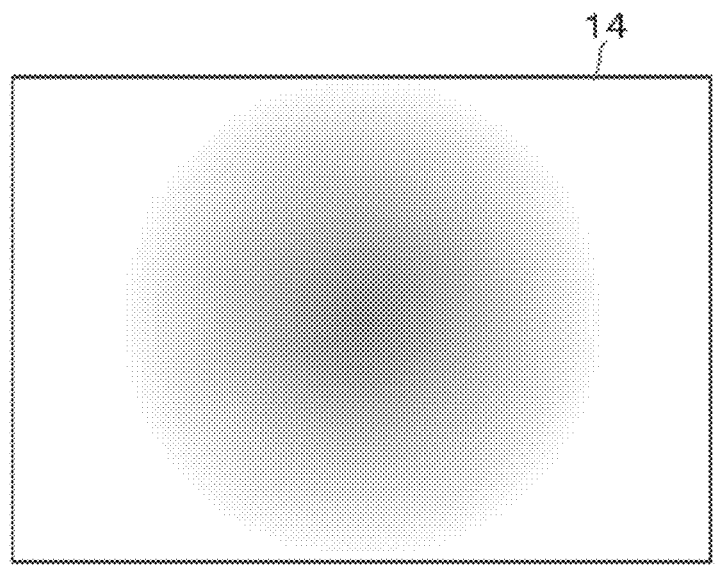
FIG. 5A is a view illustrating a case where the ND filter has a square shape.
Figure 5B:
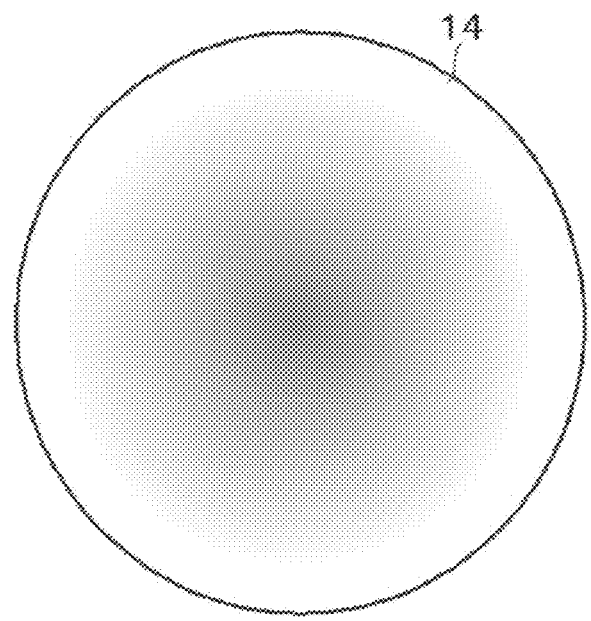
FIG. 5B is a diagram illustrating a case where the ND filter has a circular shape.

In a case where the ND filter 14 is formed on at least one of the light incident surface or the light emitting surface of the IR cut filter 13, the shape of the ND filter 14 can be formed in a rectangular shape illustrated in FIG. 5A or a circular shape illustrated in FIG. 5B. Furthermore, in a case where the ND filter 14 is formed on the lens (in a case where it is formed on at least one location of the incident surface of the condenser lens 11, the inside of the condenser lens 11, or the emitting surface of the condenser lens 11), the ND filter 14 can be formed in a circular shape as illustrated in FIG. 5B. As apparent from FIGS. 5A and 5B, the ND filter 14 has a gradation characteristic in which the light transmittance value increases from the central portion toward the peripheral portion.

Figure 6:
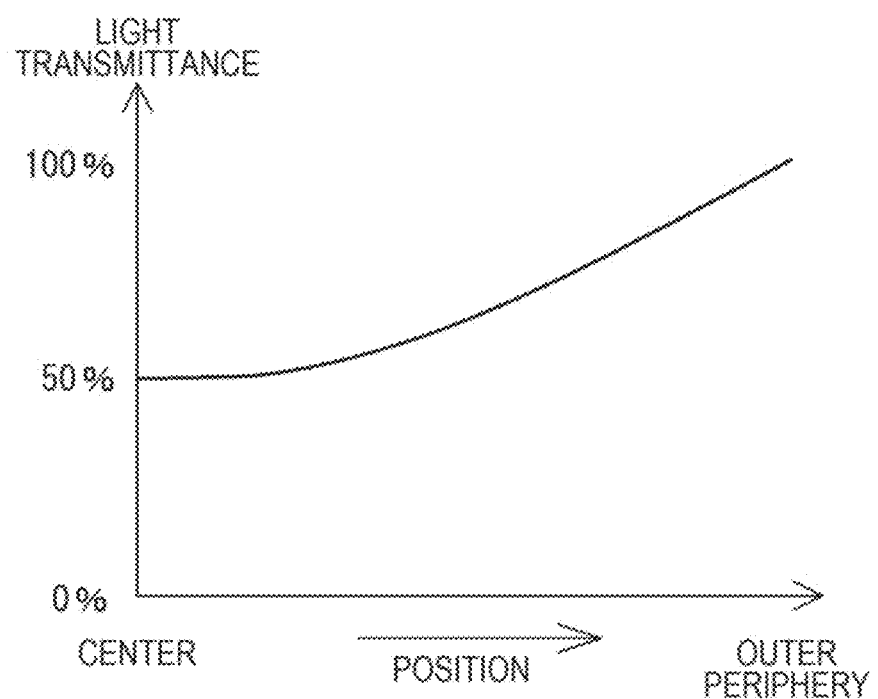
FIG. 6 is a diagram illustrating an example of a gradation characteristic of an ND filter.

An example of the gradation characteristic of the ND filter 14 is illustrated in FIG. 6. The gradation characteristic illustrated in FIG. 6 is just an example and does not limit the present technology. That is, the gradation characteristic of the ND filter 14 can be set to any characteristic in accordance with the light amount characteristic of the condenser lens 11 provided in the optical path within the imaging optical system.

Second Embodiment

Figure 7:
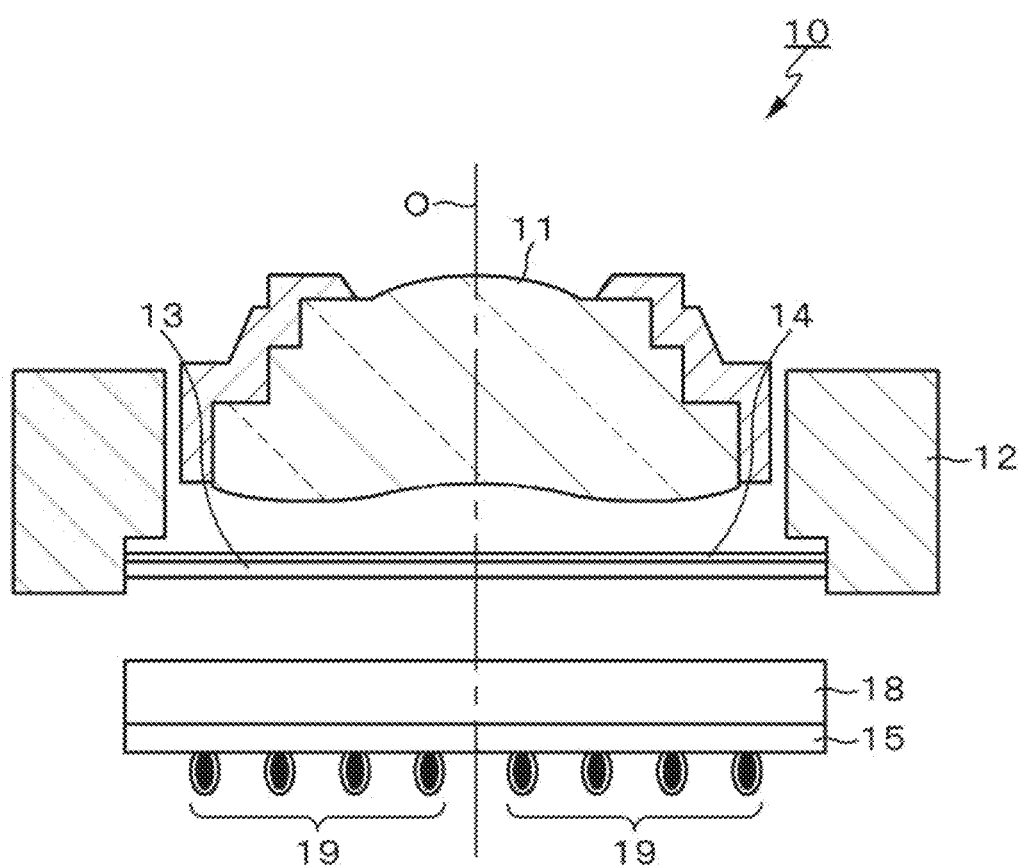
FIG. 7 is a cross-sectional view illustrating a cross-sectional structure of a camera module according to a second embodiment of the present disclosure.

A second embodiment of the present disclosure is an example of accommodating a solid-state imaging element in a package. FIG. 7 illustrates a cross-sectional structure of an imaging optical system according to the second embodiment. Similarly to the camera module according to the first embodiment, a camera module according to the second embodiment also includes the imaging optical system according to the present disclosure.

The camera module 10 according to the second embodiment differs, in configuration, from the camera module 10 according to the first embodiment having the solid-state imaging element 15 mounted on the circuit substrate 16, in that the solid-state imaging element 15 is packaged (accommodated) in a package 18 including a light-transmissive material. For the other configurations, the camera module 10 of the second embodiment is basically the same as the camera module 10 of the first embodiment. Accordingly, in the imaging optical system, the ND filter 14 preferably has a gradation characteristic in which the light transmittance value increases continuously from the optical center O (optical axis O) toward the peripheral portion (as spaced away from the optical axis O).

The package 18 for packaging the solid-state imaging element 15 is a light-transmissive material, for example, a package mainly including glass. Packaging of the solid-state imaging element 15 can be performed by using, for example, a Wafer Level Chip Size Package (WLCSP) semiconductor packaging technology that performs processes up to packaging in a wafer state. This WLCSP semiconductor packaging technology can produce the package 18 in a size of a semiconductor chip cut out from a wafer, making it possible to reduce the size and weight of the camera module 10. The package 18 accommodating the solid-state imaging element 15 is mounted on a circuit substrate via a solder bump 19.

Note that here is provided an exemplary case where the ND filter 14 is formed (deposited) on the light incident surface of the IR cut filter 13. Alternatively, however, it is possible to have a configuration in which the ND filter 14 is formed (deposited) on at least one of the light incident surface or the light emitting surface of the IR cut filter 13, as described in the first embodiment. Furthermore, the forming location is not limited to the IR cut filter 13, and it is also possible to adopt a configuration in which the ND filter 14 is formed also on at least one location out of the light incident surface of the condenser lens 11, inside the condenser lens 11, and the light emitting surface of the condenser lens 11.

Figure 8:
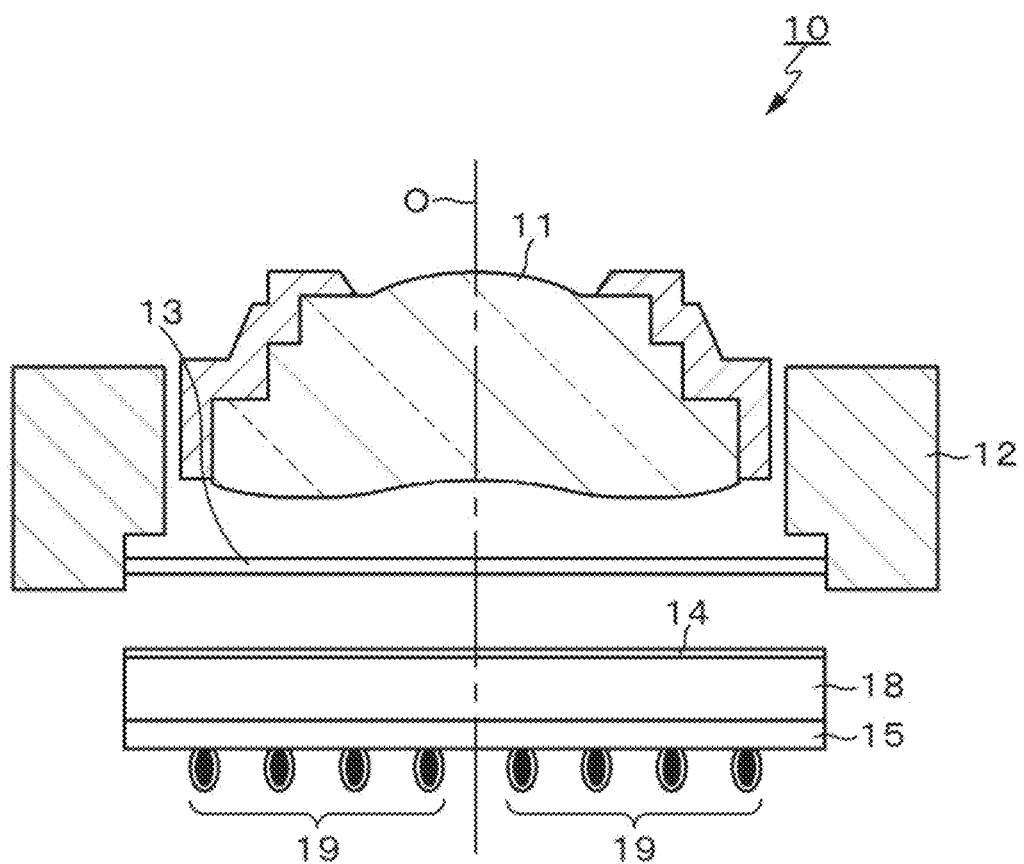
FIG. 8 is a cross-sectional view illustrating a cross-sectional structure of a camera module according to a modification of the second embodiment.

Still alternatively, in the camera module 10 according to the second embodiment, the forming location is not limited to the IR cut filter 13 and the condenser lens 11. As illustrated in FIG. 8, it is also possible to adopt a configuration in which the ND filter 14 is formed also on the imaging optical system-side surface of the package 18. Additionally, the formation position of the ND filter 14 can be appropriately changed in accordance with the characteristics, processing accuracy, and the manufacturing method of the condenser lens 11, in any of the cases where the ND filter 14 is formed on the IR cut filter 13 side, formed on the condenser lens 11 side, and formed on the package 18 side.

The camera module 10 according to the second embodiment described above can also obtain operational effects similar to the case of the camera module 10 according to the first embodiment. That is, in order to solve the problem of the small aperture diffraction of the condenser lens 11, the nonuniformity of the light amount caused by the reduction in the peripheral light amount caused by increasing the aperture of the lens can be optically corrected by the imaging optical system, rather than by correction using the signal processing that would cause problems such as emphasized noise component, emphasized flaw in the solid-state imaging element, and emphasized fine dust.

In particular, the ND filter 14 has a gradation characteristic such that the light transmittance increases together with the light amount characteristic of the condenser lens 11 from the optical center O toward the peripheral portion, making it possible to achieve uniform brightness (luminance) over the region from the optical center O toward the peripheral portion. As a result, the optical design for shading correction can be relaxed in the design of the condenser lens 11, making it possible to reduce the number of lenses constituting the condenser lens 11. Moreover, reduction in the number of lenses would lead to cost reduction and height reduction. In addition, the optical design for shading correction can be relaxed, making it possible to improve the distortion.

<Electronic Device>

The camera module according to the first embodiment and the second embodiment described above is applicable as an imaging unit (image capture portion) in an imaging apparatus such as a digital still camera or a video camera, a mobile terminal apparatus having an imaging function such as a cellular phone, or in general electronic devices such as a copier using a solid-state imaging element in an image reading part. That is, the electronic device includes a solid-state imaging element and the imaging optical system according to the first embodiment or the second embodiment.

[Imaging Apparatus]

Figure 9:
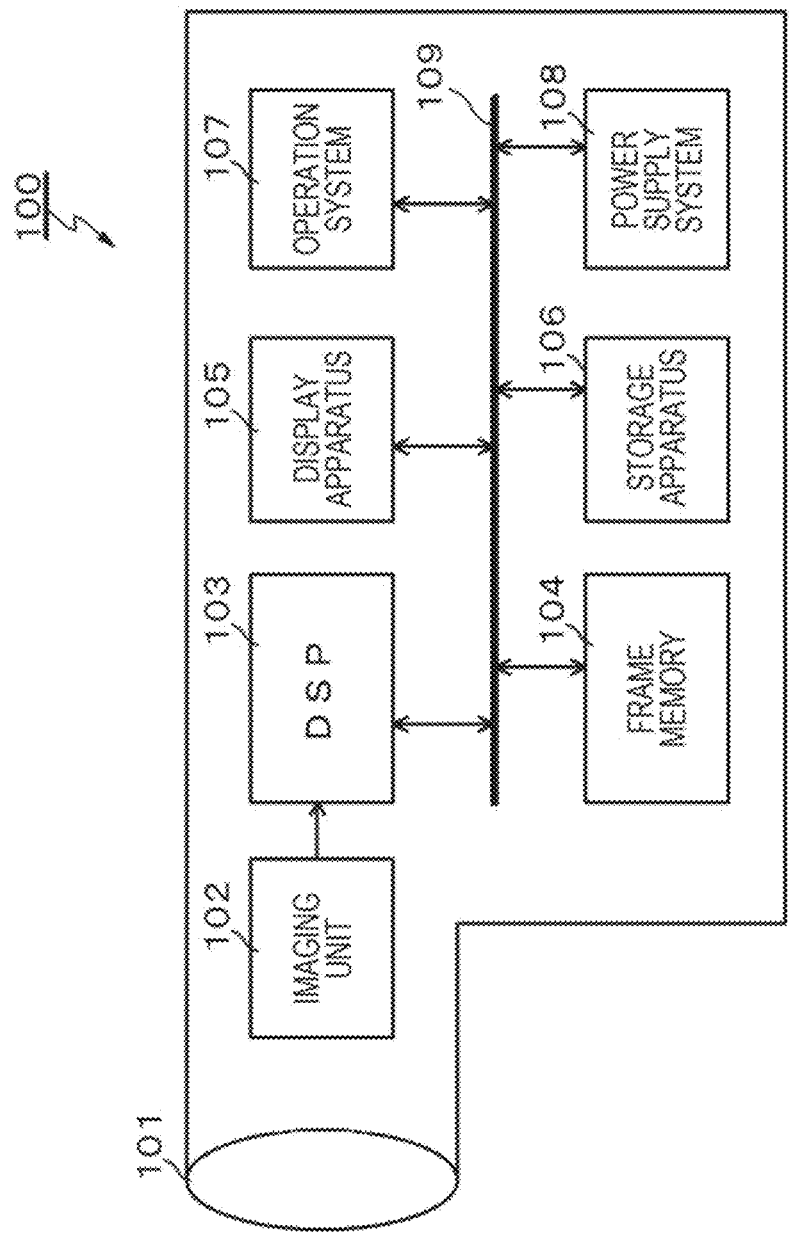
FIG. 9 is a block diagram illustrating a configuration of an imaging apparatus as an example of the electronic device of the present disclosure.

FIG. 9 is a block diagram illustrating a configuration of an imaging apparatus as an example of the electronic device of the present disclosure. As illustrated in FIG. 9, an imaging apparatus 100 according to the present example includes an imaging optical system 101, an imaging unit 102, a digital signal processor (DSP) circuit 103, a frame memory 104, a display apparatus 105, a recording apparatus 106, an operation system 107, a power supply system 108, and the like. Among these, the DSP circuit 103, the frame memory 104, the display apparatus 105, the recording apparatus 106, the operation system 107, and the power supply system 108 are mutually connected via a bus line 109.

The imaging optical system 101 captures incident light (image light) from a subject and forms an image on an imaging surface of the imaging unit 102. The imaging unit 102 converts the light amount of the incident light imaged on the imaging surface by the optical system 101 into electric signals in pixel units and outputs the electric signals as pixel signals. The DSP circuit 103 performs general camera signal processing such as white balance processing, demosaic processing, or gamma correction processing.

The frame memory 104 is used for storing data as appropriate during the signal processing in the DSP circuit 103. The display apparatus 105 is a panel type display apparatus such as a liquid crystal display apparatus or an organic electro luminescence (EL) display apparatus, and displays moving images or still images captured by the imaging unit 102. The recording apparatus 106 records the moving image or the still image captured by the imaging unit 102 on a recording medium such as a portable semiconductor memory, an optical disc, or hard disk drive (HDD).

The operation system 107 issues an operation command for various functions provided in the imaging apparatus 100 under the operation of the user. The power supply system 108 appropriately provides various types of power supply serving as operating power supply to the DSP circuit 103, the frame memory 104, the display apparatus 105, the recording apparatus 106, and the operation system 107 to these supply targets.

In the imaging apparatus 100 having the above-described configuration, the camera module according to the first embodiment or the second embodiment described above can be used as the imaging optical system 101 and the imaging unit 102. Since the camera module according to these embodiments can achieve uniform brightness over portions from the optical center to the peripheral portion, it is possible to relax the optical design of the shading correction in designing the lens of the imaging optical system 101, leading to reduction of the number of lenses.

Accordingly, with the use of the camera module according to the first embodiment or the second embodiment as the imaging optical system 101 and the imaging unit 102, it is possible to reduce the cost and the height as a result of the reduction in the number of lenses. In addition, the technology according to the present disclosure makes it possible to solve the problem of small aperture diffraction of the condenser lens, leading to achievement of miniaturization of pixels in the solid-state imaging element, thereby enabling high-definition imaging of images.

<Application Example>

The technology according to the present disclosure can be applied to various products besides the imaging apparatus such as the digital still camera and the video camera described above. For example, the technology according to the present disclosure may be applied to an endoscopic surgery system. Furthermore, the technology according to the present disclosure can be applied as a device to be mounted on any type of moving body such as an automobile, electric vehicle, hybrid electric vehicle, motorcycle, bicycle, personal mobility, airplane, drone, ship, robot, construction machine, or agricultural machine (tractor).

[Endoscopic Surgery System]

Figure 10:
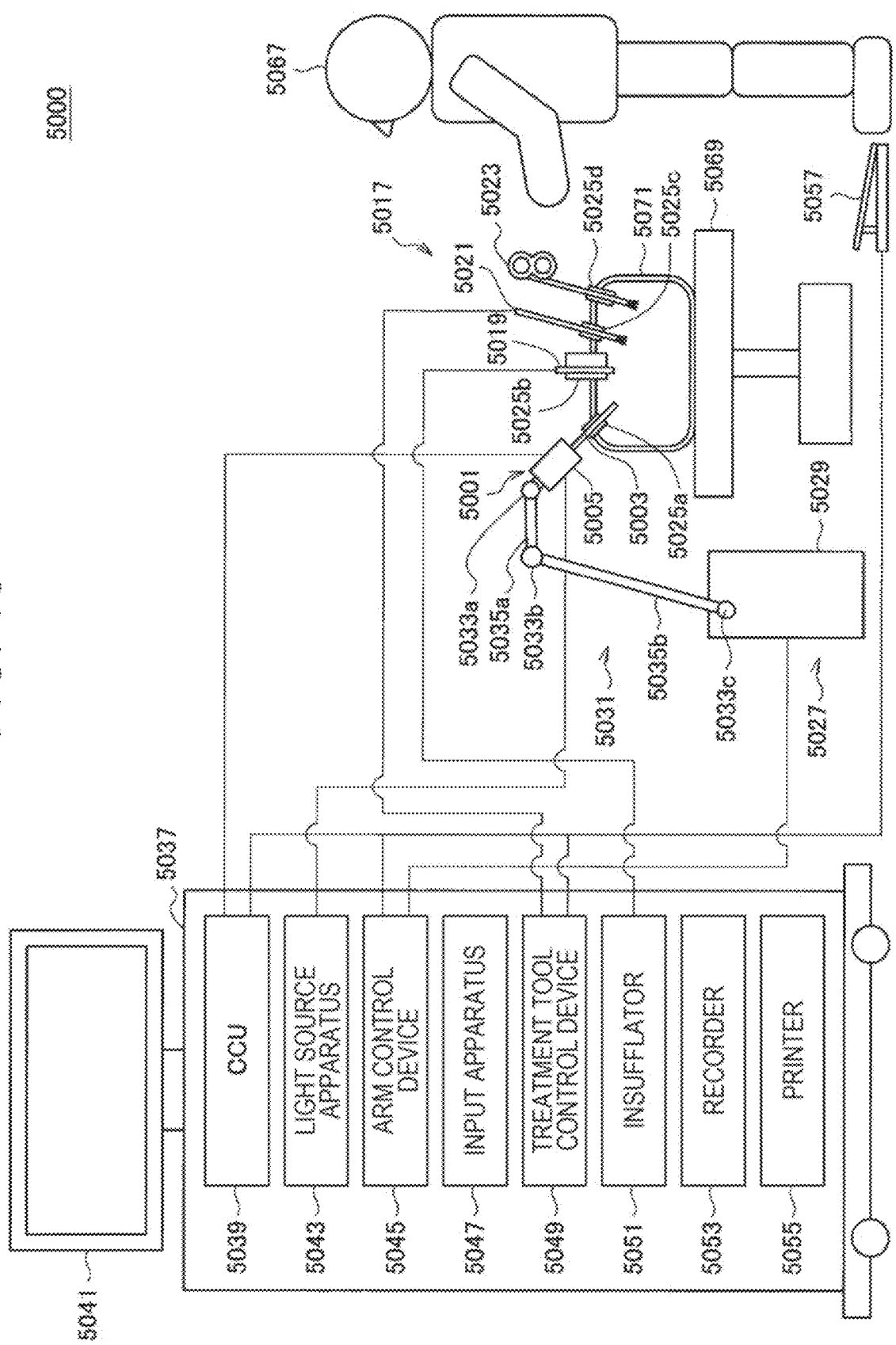
FIG. 10 is a diagram illustrating an example of a schematic configuration of an endoscopic surgery system.

FIG. 10 is a diagram illustrating an example of a schematic configuration of an endoscopic surgery system 5000 to which the technology according to the present disclosure can be applied. FIG. 10 illustrates a state where a surgeon (physician) 5067 is performing surgery on a patient 5071 on a patient bed 5069 by using the endoscopic surgery system 5000. As illustrated in the figure, the endoscopic surgery system 5000 includes an endoscope 5001, other surgical tools 5017, a support arm device 5027 for supporting the endoscope 5001, and a cart 5037 that carries various devices to be used for endoscopic surgery.

In endoscopic surgery, instead of cutting the abdominal wall and opening the abdomen, a plurality of cylindrical puncture devices called trocar 5025a to 5025d is punctured into the abdominal wall. Thereafter, a lens barrel 5003 of the endoscope 5001 and the other surgical tools 5017 are inserted into the body cavity of the patient 5071 through the trocar 5025a to 5025d. In the illustrated example, as the other surgical tools 5017, a pneumoperitoneum tube 5019, an energy treatment tool 5021, and forceps 5023 are being inserted into the body cavity of the patient 5071. In addition, the energy treatment tool 5021 is a treatment tool that performs incision and detachment of tissues, sealing of blood vessels, or the like, by using high-frequency current or ultrasonic vibration. Note that the illustrated surgical tool 5017 is merely an example, and various surgical tools generally used in endoscopic surgery, such as tweezers and a retractor, may be used as the surgical tool 5017.

An image of the surgical site in the body cavity of the patient 5071 photographed by the endoscope 5001 is displayed on a display apparatus 5041. The surgeon 5067 performs treatment such as resection of an affected site by using the energy treatment tool 5021 and the forceps 5023 while viewing the image of the surgical site displayed on the display apparatus 5041 in real time. Note that, although not illustrated, the pneumoperitoneum tube 5019, the energy treatment tool 5021, and the forceps 5023 are supported by the surgeon 5067, an assistant, or the like during the surgery.

(Support Arm Device)

The support arm device 5027 includes an arm unit 5031 extending from a base unit 5029. In the illustrated example, the arm unit 5031 is formed with joint portions 5033a, 5033b, and 5033c and links 5035a and 5035b, and is driven under the control of an arm control device 5045. The arm unit 5031 supports the endoscope 5001 and controls the position and posture of the endoscope 5001. This makes it possible to stably secure the position of the endoscope 5001.

(Endoscope)

The endoscope 5001 is formed with: a lens barrel 5003 a region of which having a predetermined length from the distal end is to be inserted into the body cavity of the patient 5071; and a camera head 5005 connected to the proximal end of the lens barrel 5003. The illustrated example illustrates the endoscope 5001 configured as a rigid scope having a rigid lens barrel 5003. Alternatively, however, the endoscope 5001 may be configured as a flexible scope having a flexible lens barrel 5003.

At the distal end of the lens barrel 5003, an opening portion into which the objective lens is fitted is provided. A light source apparatus 5043 is connected to the endoscope 5001. Light generated by the light source apparatus 5043 is guided to the distal end of the lens barrel by a light guide extending inside the lens barrel 5003, and is then applied toward an observation target in the body cavity of the patient 5071 via the objective lens. Note that the endoscope 5001 may be a forward-viewing endoscope, forward-oblique viewing endoscope, or a side-viewing endoscope.

The camera head 5005 internally includes an optical system and an imaging element. Reflected light (observation light) from the observation target is focused on the imaging element by the optical system. The observation light is photoelectrically converted by the imaging element, thereby generating an electric signal corresponding to the observation light, that is, an image signal corresponding to an observed image. The image signal is transmitted as RAW data to a camera control unit (CCU) 5039. Note that the camera head 5005 has a function of adjusting the magnification and the focal length by appropriately driving the optical system.

Note that, for example, in order to implement stereoscopic viewing (3D display) or the like, a plurality of imaging elements may be provided in the camera head 5005. In this case, a plurality of relay optical systems is provided inside the lens barrel 5003 in order to guide the observation light to each of the plurality of imaging elements.

(Various Devices Mounted on Cart)

The CCU 5039 includes a central processing unit (CPU), a graphics processing unit (GPU), and the like, and totally controls operation of the endoscope 5001 and the display apparatus 5041. Specifically, the CCU 5039 performs various types of image processing for displaying an image based on the image signal, such as development processing (demosaic processing), onto the image signal received from the camera head 5005. The CCU 5039 provides the image signal that has undergone the image processing to the display apparatus 5041. In addition, the CCU 5039 transmits a control signal to the camera head 5005 and controls driving of the camera head 5005. The control signal can include information associated with imaging conditions such as the magnification and the focal length.

Under the control of the CCU 5039, the display apparatus 5041 displays an image based on the image signal that has undergone image processing performed by the CCU 5039. In a case where the endoscope 5001 is compatible with high-resolution photography such as 4K (horizontal pixel count 3840×vertical pixel count 2160) or 8K (horizontal pixel count 7680×vertical pixel count 4320), and/or compatible with 3D display, it is possible to use the display apparatus 5041 capable of displaying in high resolution and/or capable of performing 3D display. In a case where the endoscope 5001 is compatible with high resolution photography such as 4K or 8K, it is possible to obtain deeper immersive feeling by using the display apparatus 5041 having a size of 55 inches or more. Moreover, a plurality of the display apparatuses 5041 having different resolutions and sizes may be provided depending on the application.

The light source apparatus 5043 includes a light source such as a light emitting diode (LED), for example, and supplies the irradiation light for photographing the surgical site, to the endoscope 5001.

The arm control device 5045 includes a processor such as a CPU, for example, and operates in accordance with a predetermined program, thereby controlling the driving of the arm unit 5031 of the support arm device 5027 in accordance with a predetermined control method.

The input apparatus 5047 is an input interface to the endoscopic surgery system 5000. The user can input various types of information and input instructions to the endoscopic surgery system 5000 via the input apparatus 5047. For example, the user inputs various types of information regarding surgery, such as physical information of a patient and information associated with surgical operation procedures, via the input apparatus 5047. Furthermore, via the input apparatus 5047, for example, the user inputs an instruction to drive the arm unit 5031, an instruction to change imaging conditions (type of irradiation light, the magnification, the focal length, or the like) of the endoscope 5001, an instruction to drive the energy treatment tool 5021, or the like.

The type of the input apparatus 5047 is not limited, and the input apparatus 5047 may be various types of known input apparatus. Examples of the applicable input apparatus 5047 include a mouse, a keyboard, a touch panel, a switch, a foot switch 5057, and/or a lever or the like. In a case where a touch panel is used as the input apparatus 5047, the touch panel may be provided on the display surface of the display apparatus 5041.

Alternatively, the input apparatus 5047 is a device worn by the user, such as an eyeglass type wearable device or head mounted display (HMD), for example. Various types of inputs are performed in accordance with user's gesture and line-of-sight detected by these devices. Furthermore, the input apparatus 5047 includes a camera capable of detecting the movement of the user. Various types of inputs are performed in accordance with the user's gesture and line-of-sight detected from the video image captured by the camera. Furthermore, the input apparatus 5047 includes a microphone capable of picking up the voice of the user, and various types of inputs are performed by voice through the microphone. In this manner, with a configuration of the input apparatus 5047 to be able to input various types of information in a non-contact manner, it is possible for a user (for example, the surgeon 5067) located in a clean area to perform non-contact operation a device located in a non-clean area. In addition, since the user can operate the device without releasing a hand from one's surgical tool, leading to enhancement of convenience on the user.

The treatment tool control device 5049 controls the driving of the energy treatment tool 5021 for cauterizing and dissecting tissue, sealing blood vessels, or the like. In order to inflate the body cavity of the patient 5071 to ensure a view field for the endoscope 5001 and to ensure a working space of the surgeon, an insufflator 5051 operates to inject gas into the body cavity via the pneumoperitoneum tube 5019. A recorder 5053 is a device capable of recording various types of information associated with surgery. A printer 5055 is a device capable of printing various types of information associated with surgery in various forms such as text, image, or graph.

Hereinafter, a typical configuration in the endoscopic surgery system 5000 will be described in more detail.

(Support Arm Device)

The support arm device 5027 includes the base unit 5029 as a base and the arm unit 5031 extending from the base unit 5029. In the illustrated example, the arm unit 5031 is formed with the plurality of joint portions 5033a, 5033b, and 5033c and the plurality of links 5035a and 5035b connected by the joint portion 5033b. However, for the sake of simplicity, FIG. 10 illustrates the configuration of the arm unit 5031 in a simplified manner. In practice, the shapes, the number and the arrangement of the joint portions 5033a to 5033c and the links 5035a and 5035b, the direction of the rotation axis of the joint portions 5033a to 5033c, or the like, can be appropriately set so that the arm unit 5031 has a desired degree of freedom. For example, the arm unit 5031 can be suitably configured to have four degrees of freedom of six degrees of freedom, or more. With this configuration, the endoscope 5001 can be freely moved within the movable range of the arm unit 5031, and this makes it possible to insert the lens barrel 5003 of the endoscope 5001 into the body cavity of the patient 5071 from a desired direction.

Each of the joint portions 5033a to 5033c includes an actuator. Each of the joint portions 5033a to 5033c is rotatable about a predetermined rotation axis by the drive of the actuator. The driving of the actuator is controlled by the arm control device 5045, thereby controlling the rotation angle of each of the joint portions 5033a to 5033c and controlling the driving of the arm unit 5031. This can achieve the control of the position and posture of the endoscope 5001. At this time, the arm control device 5045 can control the driving of the arm unit 5031 by various known control methods such as force control or position control.

For example, the surgeon 5067 may appropriately perform an operation input via the input apparatus 5047 (including the foot switch 5057), so as to appropriately control the driving of the arm unit 5031 by the arm control device 5045 in accordance with the operation input, leading to the control of the position and posture of the endoscope 5001. Through this control, it is possible to first allow the endoscope 5001 at the distal end of the arm unit 5031 to move from a certain position to another certain position, and then to fixedly support the endoscope 5001 at a position after the movement. Note that the arm unit 5031 may be operated by a master-slave method. In this case, the arm unit 5031 can be remotely controlled by the user via the input apparatus 5047 installed at a location away from the operating room.

Furthermore, in a case where the force control is applied, the arm control device 5045 may perform power assist control, that is, control of receiving an external force from the user, and control of driving the actuators of the individual joint portions 5033a to 5033c so as to smoothly move the arm unit 5031 in accordance with the external force. With this control, it is possible to move the arm unit 5031 with a relatively light force when the user moves the arm unit 5031 while directly touching the arm unit 5031. This makes it possible to further intuitively move the endoscope 5001 with simpler operation, leading to enhancement of convenience on the user.

Here, the endoscope 5001 is typically supported by a doctor called an endoscopist in endoscopic surgery. In contrast, with the use of the support arm device 5027, it is possible to reliably secure the position of the endoscope 5001 without manual work, leading to stable acquisition of an image of the surgical site and smooth execution of surgery.

Note that the arm control device 5045 is not necessarily provided in the cart 5037. Furthermore, the arm control device 5045 is not necessarily one device. For example, the arm control device 5045 may be provided in each of the joint portions 5033a to 5033c of the arm unit 5031 of the support arm device 5027, and the plurality of arm control devices 5045 cooperate with each other to achieve drive of the arm unit 5031.

(Light Source Apparatus)

The light source apparatus 5043 supplies the endoscope 5001 with irradiation light for photographing a surgical site. The light source apparatus 5043 is formed with, for example, an LED, a laser light source, or a white light source constituted by a combination of these. At this time, in a case where the white light source is constituted with the combination of the RGB laser light sources, it is possible to control the output intensity and the output timing of individual colors (individual wavelengths) with high accuracy. Accordingly, it is possible to perform white balance adjustment of the captured image on the light source apparatus 5043.

Moreover, in this case, by emitting the laser light from each of the RGB laser light sources to an observation target on the time-division basis and by controlling the driving of the imaging element of the camera head 5005 in synchronization with the light emission timing, it is possible to capture the image corresponding to each of RGB on the time-division basis. According to this method, a color image can be obtained without a color filter provided in the imaging element.

In addition, the driving of the light source apparatus 5043 may be controlled so as to change the output light intensity at every predetermined time. With the control of the driving of the imaging element of the camera head 5005 in synchronization with the timing of the change of the intensity of the light so as to obtain images on the time-division basis and combine the images, it is possible to generate an image with high dynamic range without blocked up shadows or blown out highlights.

Furthermore, the light source apparatus 5043 may be configured to be able to supply light of a predetermined wavelength band corresponding to special light observation. The special light observation is used to perform narrowband light observation (narrow band imaging). The narrowband light observation uses the wavelength dependency of the light absorption in the body tissue and emits light in a narrower band compared with the irradiation light (that is, white light) at normal observation, thereby photographing a predetermined tissue such as a blood vessel of the mucosal surface layer with high contrast. Alternatively, the special light observation may perform fluorescence observation to obtain an image by fluorescence generated by emission of excitation light. Fluorescence observation can be performed to observe fluorescence emitted from a body tissue to which excitation light is applied (autofluorescence observation), and can be performed with local administration of reagent such as indocyanine green (ICG) to the body tissue, and together with this, excitation light corresponding to the fluorescence wavelength of the reagent is emitted to the body tissue to obtain a fluorescent image, or the like. The light source apparatus 5043 can be configured to be able to supply narrowband light and/or excitation light corresponding to such special light observation.

(Camera Head and CCU)

Figure 11:
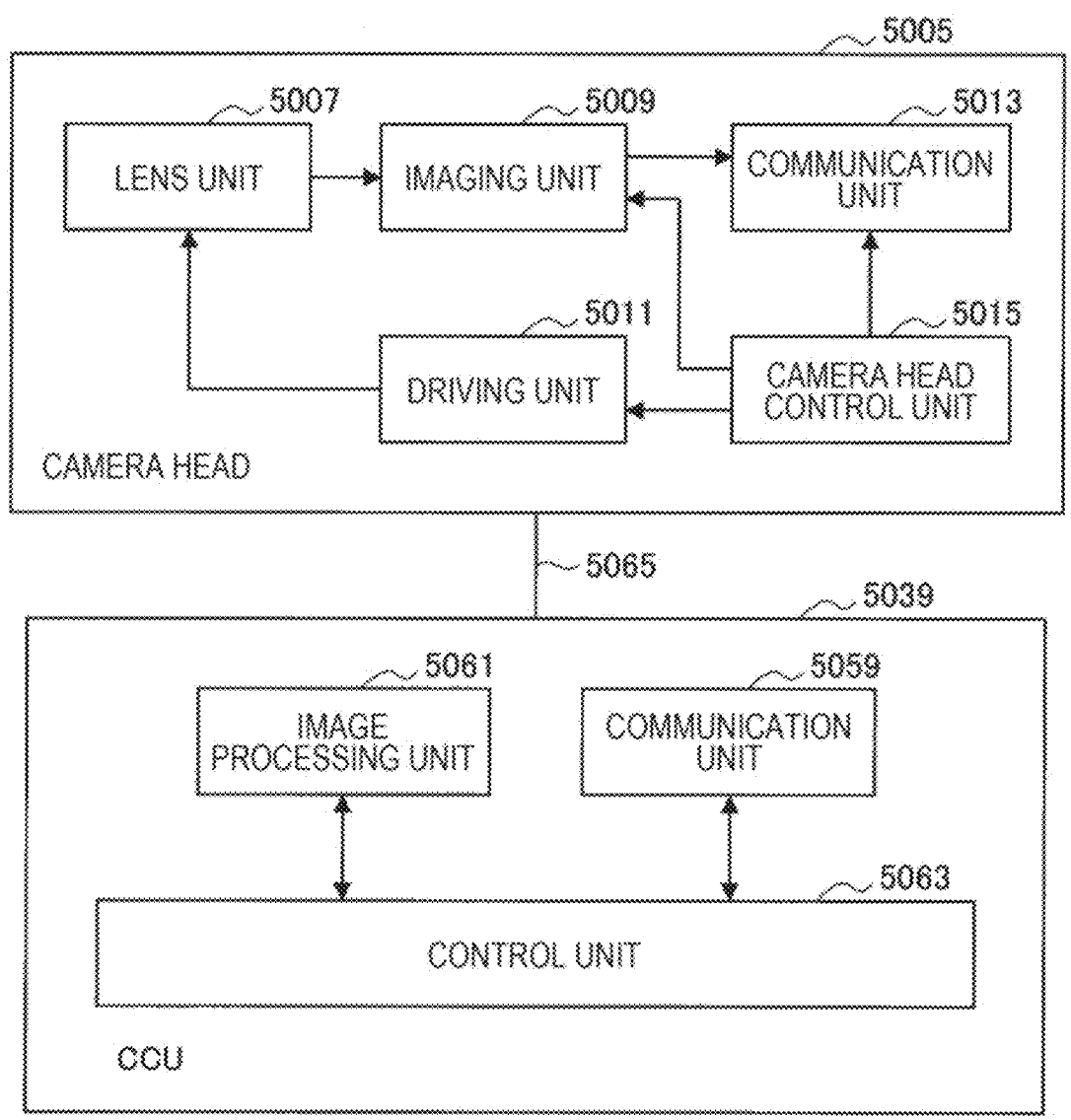
FIG. 11 is a block diagram illustrating an example of a functional configuration of a camera head and the CCU illustrated in FIG. 10.

Functions of camera head 5005 and CCU 5039 of the endoscope 5001 will be described in more detail with reference to FIG. 11. FIG. 11 is a block diagram illustrating an example of a functional configuration of the camera head 5005 and the CCU 5039 illustrated in FIG. 10.

Referring to FIG. 11, the camera head 5005 includes, as a functional configuration, a lens unit 5007, an imaging unit 5009, a driving unit 5011, a communication unit 5013, and a camera head control unit 5015. In addition, the CCU 5039 includes, as a functional configuration, a communication unit 5059, an image processing unit 5061, and a control unit 5063. The camera head 5005 and the CCU 5039 are connected with each other by a transmission cable 5065 so as to enable bi-directional communication.

First, the functional configuration of the camera head 5005 will be described. The lens unit 5007 is an optical system provided at a connecting portion with the lens barrel 5003. The observation light captured from the distal end of the lens barrel 5003 is guided to the camera head 5005 and enters the lens unit 5007. The lens unit 5007 is formed by combining a plurality of lenses including a zoom lens and a focus lens. Optical characteristics of the lens unit 5007 are adjusted so as to collect the observation light on a light receiving surface of the imaging element of the imaging unit 5009. In addition, the zoom lens and the focus lens are configured so that their positions on the optical axis can move in order to adjust the magnification and focus of the captured image.

The imaging unit 5009 includes an imaging element, and is arranged at a subsequent stage of the lens unit 5007. The observation light having passed through the lens unit 5007 is focused on the light receiving surface of the imaging element, and an image signal corresponding to the observation image is generated by photoelectric conversion. The image signal generated by the imaging unit 5009 is supplied to the communication unit 5013.

An example of the imaging element constituting the imaging unit 5009 is an image sensor of a complementary metal oxide semiconductor (CMOS) type having Bayer arrangement and capable of color photography. Note that the imaging element may be an imaging element capable of handling photography of a high resolution image of 4K or more. With acquisition of the image of the surgical site with high resolution, the surgeon 5067 can grasp states of the surgical site in more detail, leading to smooth progress the operation.

In addition, the imaging element constituting the imaging unit 5009 includes a pair of imaging elements for acquisition of image signals for right eye and left eye corresponding to 3D display. With implementation of 3D display, the surgeon 5067 can grasp the depth of the living tissue in the surgical site with higher accuracy. Note that in a case where the imaging unit 5009 is formed in a multi-plate type, a plurality of lens units 5007 is also provided corresponding to each of the imaging elements.

In addition, the imaging unit 5009 is not necessarily provided in the camera head 5005. For example, the imaging unit 5009 may be provided inside the lens barrel 5003 just behind the objective lens.

The driving unit 5011 includes an actuator and moves the zoom lens and the focus lens of the lens unit 5007 by a predetermined distance along the optical axis under the control of the camera head control unit 5015. With this operation, the magnification and focus of the image captured by the imaging unit 5009 can be appropriately adjusted.

The communication unit 5013 includes a communication apparatus for transmitting and receiving various types of information to and from the CCU 5039. The communication unit 5013 transmits the image signal obtained from the imaging unit 5009 as RAW data to the CCU 5039 via the transmission cable 5065. At this time, it is preferable that the image signal be transmitted by optical communication in order to display the captured image of the surgical site with low latency. At the time of surgery, the surgeon 5067 performs surgery while observing the state of the affected site through the captured image. Accordingly, it is highly preferable to be able to display a dynamic image of the surgical site in real time as much as possible in order to achieve safer and more reliable surgery. In a case where optical communication is performed, a photoelectric conversion module that converts an electric signal into an optical signal is provided in the communication unit 5013. The image signal is converted into an optical signal by the photoelectric conversion module, and then transmitted to the CCU 5039 via the transmission cable 5065.

Furthermore, the communication unit 5013 receives a control signal for controlling driving of the camera head 5005 from the CCU 5039. The control signal includes information associated with imaging conditions, such as information designating a frame rate of a captured image, information designating an exposure value at the time of imaging, and/or information designating the magnification and focus of the captured image. The communication unit 5013 supplies the received control signal to the camera head control unit 5015. Note that the control signal from the CCU 5039 may also be transmitted by optical communication. In this case, the communication unit 5013 includes a photoelectric conversion module that converts the optical signal into an electric signal, and the control signal is converted to an electric signal by the photoelectric conversion module, and is then supplied to the camera head control unit 5015.

Note that the imaging conditions such as the above frame rate, exposure value, magnification, and focus are automatically set by the control unit 5063 of the CCU 5039 on the basis of the acquired image signal. That is, an auto exposure (AE) function, an auto focus (AF) function, and an auto white balance (AWB) function are mounted on the endoscope 5001.

The camera head control unit 5015 controls driving of the camera head 5005 on the basis of a control signal from the CCU 5039 received via the communication unit 5013 For example, the camera head control unit 5015 controls driving of the imaging element of the imaging unit 5009 on the basis of information designating the frame rate of the captured image and/or information designating exposure at the time of imaging. In addition, the camera head control unit 5015 appropriately moves the zoom lens and the focus lens of the lens unit 5007 via the driving unit 5011 on the basis of the information designating the magnification and focus of the captured image. The camera head control unit 5015 may further include a function of storing information for identifying the lens barrel 5003 and the camera head 5005.

Note that providing the configuration of the lens unit 5007, the imaging unit 5009, or the like, in a hermetically sealed structure having high airtightness and waterproofness would make it possible to allow the camera head 5005 to have resistance to autoclave sterilization processing.

Next, a functional configuration of the CCU 5039 will be described. The communication unit 5059 includes a communication apparatus for transmitting and receiving various types of information to and from the camera head 5005. The communication unit 5059 receives the image signal transmitted from the camera head 5005 via the transmission cable 5065. At this time, as described above, the image signal can be suitably transmitted by optical communication. In this case, the communication unit 5059 includes a photoelectric conversion module that converts an optical signal into an electric signal, corresponding to the optical communication. The communication unit 5059 supplies the image signal converted into the electric signal to the image processing unit 5061.

Furthermore, the communication unit 5059 transmits a control signal for controlling the driving of the camera head 5005 to the camera head 5005. The control signal may also be transmitted by optical communication.

The image processing unit 5061 performs various types of image processing on the image signal in RAW data transmitted from the camera head 5005. Examples of the image processing include various types of known signal processing such as developing processing, high image quality processing (band enhancement processing, super resolution processing, noise reduction (NR) processing and/or camera shake correction processing, for example), and/or enlargement processing (electronic zoom processing). Furthermore, the image processing unit 5061 performs demodulation processing on image signals for performing AE, AF, and AWB.

The image processing unit 5061 includes a processor such as a CPU and a GPU. The processor operates in accordance with a predetermined program to enable execution of the above-described image processing and demodulation processing. Note that in a case where the image processing unit 5061 includes a plurality of GPUs, the image processing unit 5061 appropriately divides the information associated with the image signals and performs image processing in parallel by the plurality of GPUs.

The control unit 5063 performs various types of control related to imaging of a surgical site by the endoscope 5001 and display of the captured image. For example, the control unit 5063 generates a control signal for controlling the driving of the camera head 5005. At this time, in a case where the imaging condition is input by the user, the control unit 5063 generates the control signal on the basis of the input by the user. Alternatively, in a case where the endoscope 5001 includes the AE function, the AF function, and the AWB function, the control unit 5063 appropriately calculates the optimum exposure value, a focal length, and white balance in accordance with a result of demodulation processing performed by the image processing unit 5061, and generates a control signal.

In addition, the control unit 5063 causes the display apparatus 5041 to display the image of the surgical site on the basis of the image signal that has undergone image processing by the image processing unit 5061. At this time, the control unit 5063 recognizes various objects in the surgical site image by using various image recognition techniques. For example, the control unit 5063 detects the shape, color, or the like of the edge of an object included in the surgical site image, thereby making it possible to recognize a surgical tool such as forceps, a specific living body site, bleeding, a mist at the time of using the energy treatment tool 5021, or the like. When displaying the image of the operation site on the display apparatus 5041, the control unit 5063 superimposes and displays various surgical operation support information on the image of the surgical site by using the recognition result. Surgical support information is superimposed and displayed, and presented to the surgeon 5067, thereby making it possible to proceed with surgery more safely and reliably.

The transmission cable 5065 connecting the camera head 5005 and the CCU 5039 is an electric signal cable compatible with electric signal communication, an optical fiber compatible with optical communication, or a composite cable of these.

Here, while the example illustrated in the drawing is a case of performing wired communication using the transmission cable 5065, communication between the camera head 5005 and the CCU 5039 may be performed wirelessly. In a case where the communication between the two units is performed wirelessly, there is no need to install the transmission cable 5065 in the operating room, making it possible to eliminate a situation in which the movement of the medical staff in the operating room is hindered by the transmission cable 5065.

An example of the endoscopic surgery system 5000 to which the technology according to the present disclosure can be applied has been described above. Note that although the endoscopic surgery system 5000 has been described as an example here, the system to which the technology according to the present disclosure can be applied is not limited to this example. For example, the technology according to the present disclosure may be applied to a flexible endoscope system for examination or a microscopic surgery system.

The technology according to the present disclosure can be suitably applied to the camera head 5005 out of the above-described configuration. Specifically, the camera module according to the first embodiment or the second embodiment as described above can be used as the optical system and the imaging element provided inside the camera head 5005, more specifically, as the lens unit 5007 and the imaging unit 5009. Application of the technology according to the present disclosure to the camera head 5005 would reduce the number of lenses of the optical system, and this would lead to reduction of the cost of the camera head 5005 and the cost of the endoscopic surgery system 5000. Furthermore, since the problem of the small aperture diffraction of the lens of the optical system can be solved by the technology according to the present disclosure, it is possible to miniaturize pixels of the imaging element. As a result, it is possible to obtain a high-definition image, so that surgery can be performed more safely and more reliably.

[Device Mounted on Mobile Unit]

Figure 12:
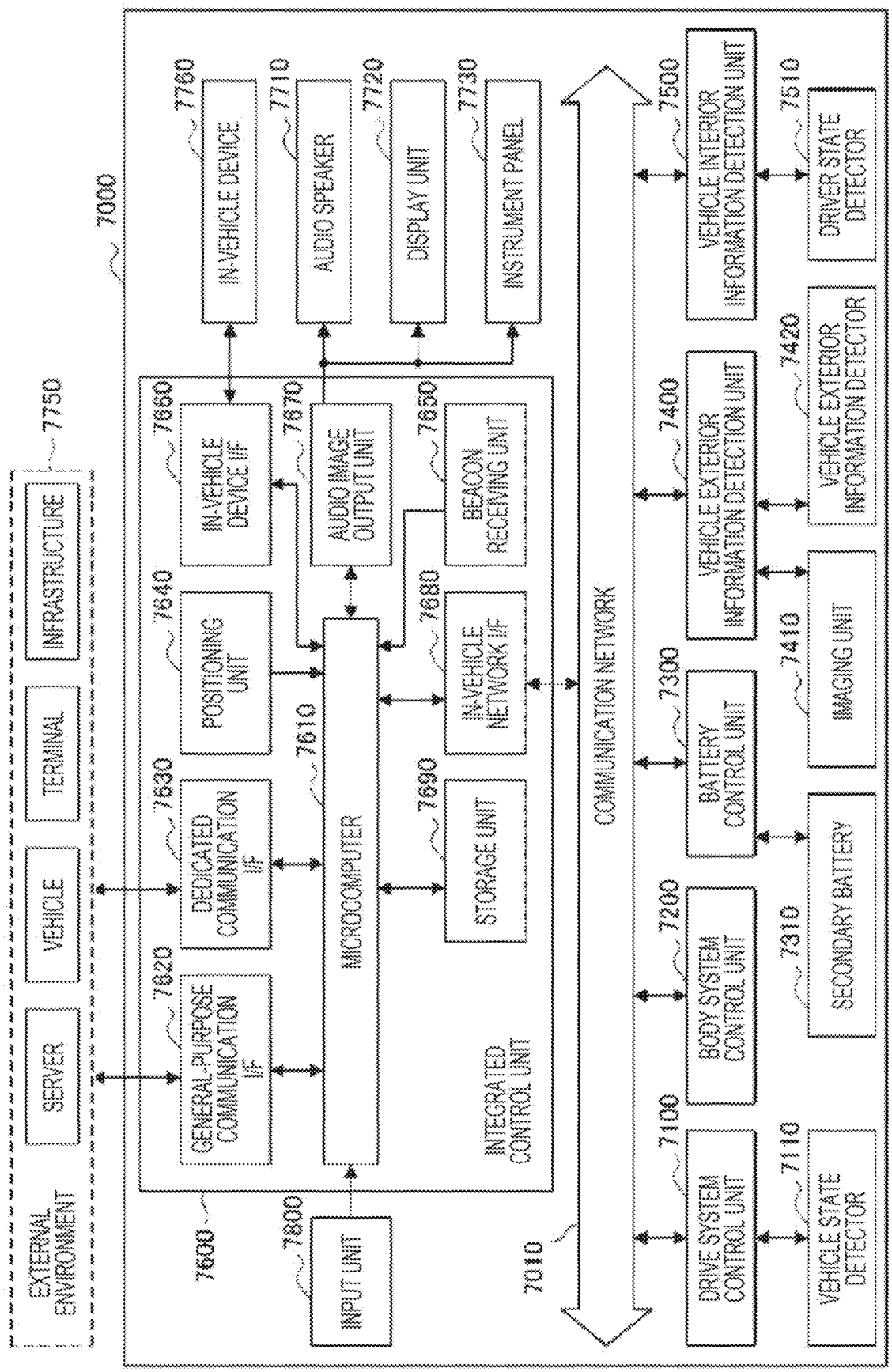
FIG. 12 is a block diagram illustrating a schematic configuration example of a vehicle control system.

FIG. 12 is a block diagram illustrating an example of a schematic configuration of a vehicle control system 7000 as an example of a moving body control system to which the technology according to the present disclosure can be applied. The vehicle control system 7000 includes a plurality of electronic control units connected via a communication network 7010. In the example illustrated in FIG. 12, the vehicle control system 7000 includes a drive system control unit 7100, a body system control unit 7200, a battery control unit 7300, an vehicle exterior information detection unit 7400, an vehicle interior information detection unit 7500, and an integrated control unit 7600. The communication network 7010 connecting the plurality of control units may be an in-vehicle communication network conforming to a certain standard such as a Controller Area Network (CAN), a Local Interconnect Network (LIN), a Local Area Network (LAN), or FlexRay (registered trademark), for example.

Each of the control units includes: a microcomputer that performs arithmetic processing in accordance with various programs; a storage unit that stores programs executed by the microcomputer, parameters used for various calculations, or the like; and a drive circuit that drives devices to be controlled. Each of the control units includes: a network I/F for communicating with another control unit via the communication network 7010; and a communication I/F for performing communication with internal or external devices of the vehicle, a sensor, or the like, using wired communication or wireless communication. FIG. 12 illustrates, as a functional configuration of the integrated control unit 7600, units such as a microcomputer 7610, a general-purpose communication I/F 7620, a dedicated communication I/F 7630, a positioning unit 7640, a beacon receiving unit 7650, an in-vehicle device I/F 7660, an audio image output unit 7670, an in-vehicle network I/F 7680, and a storage unit 7690. Similarly, the other control units include a microcomputer, a communication I/F, a storage unit, or the like.

The drive system control unit 7100 controls operation of the apparatus related to the drive system of the vehicle in accordance with various programs. For example, the drive system control unit 7100 functions as a control apparatus of a driving force generation apparatus that generates a driving force of a vehicle such as an internal combustion engine or a driving motor, a driving force transmission mechanism that transmits a driving force to the wheels, a steering mechanism that adjusts steering angle of the vehicle, a braking apparatus that generates a braking force of the vehicle, or the like. The drive system control unit 7100 may have a function as a control apparatus such as Antilock Brake System (ABS), or Electronic Stability Control (ESC).

The drive system control unit 7100 is connected with a vehicle state detector 7110. The vehicle state detector 7110 includes at least one of: a gyro sensor that detects angular velocity of the rotational motion of the vehicle body; an acceleration sensor that detects acceleration of the vehicle; or a sensor for detection an operation amount of the accelerator pedal, an operation amount of the brake pedal, steering angle of the steering wheel, and an engine rotation speed, a wheel rotation speed, or the like, for example. The drive system control unit 7100 performs arithmetic processing by using a signal input from the vehicle state detector 7110 so as control the internal combustion engine, the drive motor, the electric power steering device, the brake device, or the like.

The body system control unit 7200 controls operation of various devices equipped on the vehicle body in accordance with various programs. For example, the body system control unit 7200 functions as a control apparatus for a keyless entry system, a smart key system, a power window device, or various lamps such as a head lamp, a back lamp, a brake lamp, a turn signal lamp, or a fog lamp. In this case, the body system control unit 7200 can receive inputs of a radio wave transmitted from a portable device that substitutes a key, or a signal of various switches. The body system control unit 7200 receives inputs of these radio waves or signals and controls the door lock device, the power window device, the lamp, etc. of the vehicle.

The battery control unit 7300 controls a secondary battery 7310 being a power supply source for the driving motor in accordance with various programs. For example, the battery control unit 7300 receives an input of information such as battery temperature, the battery output voltage, or the remaining battery capacity from a battery apparatus including the secondary battery 7310. The battery control unit 7300 performs arithmetic processing by using these signals so as to perform temperature adjustment control of the secondary battery 7310 or control of the cooling device or the like included in the battery apparatus.

The vehicle exterior information detection unit 7400 detects information outside the vehicle equipped with the vehicle control system 7000. For example, the vehicle exterior information detection unit 7400 is connected to at least one of an imaging unit 7410 or a vehicle exterior information detector 7420. The imaging unit 7410 includes at least one of a Time-of-flight (ToF) camera, a stereo camera, a monocular camera, an infrared camera, or other camera. For example, the vehicle exterior information detector 7420 includes at least one of: an environmental sensor that detects current weather or climate, or an ambient information detection sensor that detects another vehicle, an obstacle, a pedestrian, or the like, surrounding the vehicle equipped with the vehicle control system 7000.

The environmental sensor may be, for example, at least one of a raindrop sensor for detecting rain, a fog sensor for detecting mist, a sunshine sensor for detecting sunshine degree, or a snow sensor for detecting snowfall. The ambient information detection sensor may be at least one of an ultrasonic sensor, a radar apparatus, or a light detection and ranging/laser imaging detection and ranging (LIDAR) apparatus. The imaging unit 7410 and the vehicle exterior information detector 7420 may be each provided as independent sensors or devices, or may be provided as a device integrating a plurality of sensors or devices.

Figure 13:
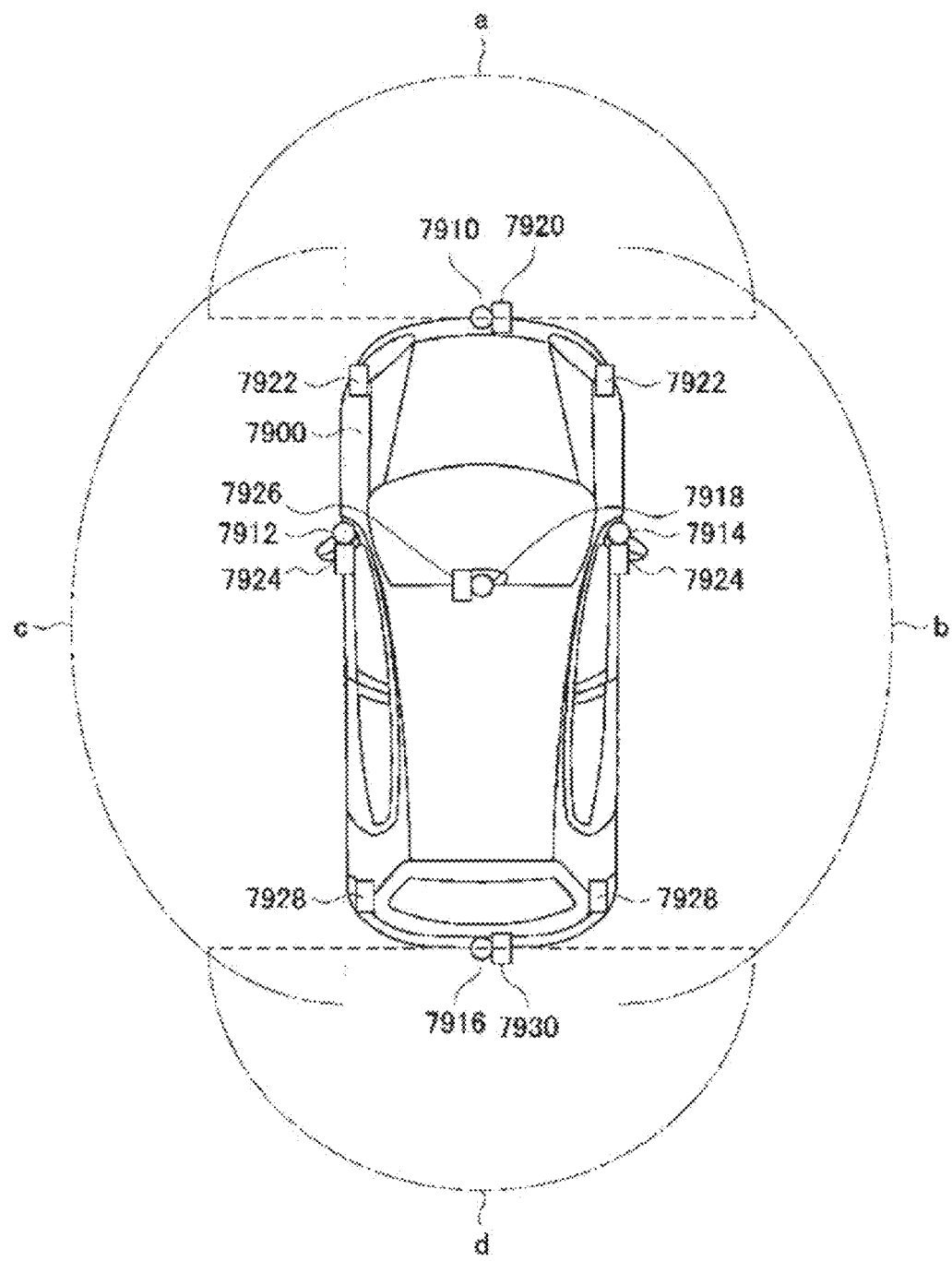
FIG. 13 is an explanatory diagram illustrating an example of installation positions of a vehicle exterior information detector and an imaging unit.

Here, FIG. 13 illustrates an example of installation positions of the imaging unit 7410 and the vehicle exterior information detector 7420. For example, imaging units 7910, 7912, 7914, 7916, and 7918 are provided in at least one of positions on a vehicle 7900, including a nose, a side mirror, a rear bumper, a rear door, or an upper portion of windshield in a passenger compartment. The imaging unit 7910 provided at a nose and the imaging unit 7918 provided on the upper portion of the windshield in the passenger compartment mainly obtain an image ahead of the vehicle 7900. The imaging units 7912 and 7914 provided at the side mirror mainly obtain images of the side of the vehicle 7900. The imaging unit 7916 provided in the rear bumper or the back door mainly obtains an image behind the vehicle 7900. The imaging unit 7918 provided at an upper portion of the windshield in the passenger compartment is mainly used for detecting a preceding vehicle, a pedestrian, an obstacle, a traffic signal, a traffic sign, a lane, or the like.

Note that FIG. 13 illustrates an example of photographing ranges of each of the imaging units 7910, 7912, 7914, and 7916. An imaging range a represents an imaging range of the imaging unit 7910 provided at the nose, imaging ranges b and c represent imaging ranges of the imaging units 7912 and 7914 provided at the side mirror, and an imaging range d represents an imaging range of the imaging unit 7916 provided at the rear bumper or the back door. For example, the image data captured by the imaging units 7910, 7912, 7914, or 7916 are superimposed to obtain an overhead view image of the vehicle 7900 viewed from above.

Each of the vehicle exterior information detectors 7920, 7922, 7924, 7926, 7928, and 7930 provided on the front, rear, side, corner, and an upper portion of the windshield in the passenger compartment, of the vehicle 7900, may be an ultrasonic sensor or a radar apparatus, for example. The vehicle exterior information detectors 7920, 7926, and 7930 provided on the nose, the rear bumper, the back door, and an upper portion of the windshield in the passenger compartment, of the vehicle 7900, may be LIDAR apparatuses, for example. The vehicle exterior information detectors 7920 to 7930 are mainly used for detecting a preceding vehicle, a pedestrian, an obstacle, or the like.

Returning to FIG. 12, the description will be continued. The vehicle exterior information detection unit 7400 causes the imaging unit 7410 to capture an image of the outside of the vehicle and receives the captured image data. Furthermore, the vehicle exterior information detection unit 7400 receives detection information from the connected vehicle exterior information detector 7420. In a case where the vehicle exterior information detector 7420 is an ultrasonic sensor, a radar apparatus, or an LIDAR apparatus, the vehicle exterior information detection unit 7400 causes ultrasonic waves, electromagnetic waves, or the like to be transmitted, and receives information of the received reflected waves. The vehicle exterior information detection unit 7400 may perform object detection processing or distance detection processing on objects such as a person, a car, an obstacle, a sign, and a character on a road surface on the basis of the received information. The vehicle exterior information detection unit 7400 may perform environment recognition processing of recognizing rainfall, fog, road surface condition, or the like, on the basis of the received information. The vehicle exterior information detection unit 7400 may calculate the distance to the object outside the vehicle on the basis of the received information.

Furthermore, the vehicle exterior information detection unit 7400 may perform image recognition processing or distance detection processing of recognizing people, cars, obstacles, signs, characters on a road surface, or the like, on the basis of the received image data. The vehicle exterior information detection unit 7400 may perform processing such as distortion correction or alignment on the received image data and may combine the image data captured by mutually different imaging units 7410 to generate an overhead view image or a panoramic image. The vehicle exterior information detection unit 7400 may perform viewpoint conversion processing by using image data captured by mutually different imaging units 7410.

The vehicle interior information detection unit 7500 detects information inside the vehicle. The vehicle interior information detection unit 7500 is connected with a driver state detector 7510 that detects the state of the driver, for example. The driver state detector 7510 may include a camera that images the driver, a biometric sensor that detects biological information of the driver, a microphone that collects sounds in the passenger compartment, or the like. The biometric sensor is provided on a seating surface, a steering wheel, or the like, for example, and detects biological information of an occupant sitting on a seat or a driver holding a steering wheel. The vehicle interior information detection unit 7500 may calculate the degree of fatigue or the degree of concentration of the driver or may judge whether the driver is dozing off on the basis of the detection information input from the driver state detector 7510. The vehicle interior information detection unit 7500 may perform noise canceling processing or the like on collected audio signals.

The integrated control unit 7600 controls the overall operation within the vehicle control system 7000 in accordance with various programs. The integrated control unit 7600 is connected with an input unit 7800. The input unit 7800 is implemented by an apparatus which can be operated by an input of an occupant, such as a touch screen, a button, a microphone, a switch, or a lever, for example. The integrated control unit 7600 may receive input of data obtained by performing speech recognition on the sound input by the microphone. The input unit 7800 may be, for example, a remote control device using infrared rays or other radio waves, or an external connection device such as a cellular phone or a personal digital assistant (PDA) compatible with the operation of the vehicle control system 7000. The input unit 7800 may be a camera, for example, in which case the occupant can input information by gesture. Alternatively, data obtained by detecting the movement of the wearable device worn by the occupant may be input. Furthermore, the input unit 7800 may include, for example, an input control circuit or the like that generates an input signal on the basis of information input by an occupant or the like using the above input unit 7800 and outputs the generated input signal to the integrated control unit 7600. The occupant or the like operates the input unit 7800 so as to input various data or give an instruction on processing operation to the vehicle control system 7000.

The storage unit 7690 may include read only memory (ROM) that stores various programs to be executed by the microcomputer, and a random access memory (RAM) that stores various parameters, calculation results, sensor values, or the like. Furthermore, the storage unit 7690 may be implemented by a magnetic storage device such as a hard disc drive (HDD), a semiconductor storage device, an optical storage device, a magneto-optical storage device, or the like.

The general-purpose communication I/F 7620 is a general-purpose communication I/F that mediates communication with various devices existing in external environment 7750. The general-purpose communication I/F 7620 may include a cellular communication protocol such as Global System of Mobile communications (GSM) (registered trademark), WiMAX, Long Term Evolution (LTE) or LTE-Advanced (LTE-A), or other wireless communication protocols such as a wireless LAN (also referred to as Wi-Fi (registered trademark)) and Bluetooth (registered trademark). The general-purpose communication I/F 7620 may be connected to a device (for example, an application server or a control server) existing on an external network (for example, the Internet, a cloud network, or a company specific network) via a base station or an access point, for example. Furthermore, the general-purpose communication I/F 7620 may use Peer To Peer (P2P) technology, for example, to connect to a terminal (for example, a terminal of a pedestrian or a shop, or a machine type communication (MTC) terminal) existing in the vicinity of the vehicle.

The dedicated communication I/F 7630 is a communication I/F that supports a communication protocol formulated for the purpose of being used in a vehicle. For example, the dedicated communication I/F 7630 may implement a standard protocol such as Wireless Access in Vehicle Environment (WAVE) or Dedicated Short Range Communications (DSRC), which is a combination of lower layer IEEE 802.11p and upper layer IEEE 1609, or a cellular communication protocol. Typically, the dedicated communication I/F 7630 implements V2X communication which is a concept including one or more of Vehicle to Vehicle communication, Vehicle to Infrastructure communication, Vehicle to Home communication, and Vehicle to Pedestrian communication.

The positioning unit 7640 receives, for example, a Global Navigation Satellite System (GNSS) signal from a GNSS satellite (for example, a Global Positioning System (GPS) signal from a GPS satellite) and executes positioning, and then, generates position information including the latitude, longitude, and altitude of the vehicle. Note that the positioning unit 7640 may specify a current position by exchanging signals with a wireless access point or may obtain the position information from a terminal such as a cellular phone, a PHS, or a smartphone, having a positioning function.

For example, the beacon receiving unit 7650 receives radio waves or electromagnetic waves transmitted from a radio station or the like installed on a road and obtains information such as the current position, congestion, closing of a road, or required time. Note that the function of the beacon receiving unit 7650 may be included in the dedicated communication I/F 7630 described above.

The in-vehicle device I/F 7660 is a communication interface that mediates connection between the microcomputer 7610 and various in-vehicle devices 7760 existing in a vehicle. The in-vehicle device I/F 7660 may establish a wireless connection using a wireless communication protocol such as wireless LAN, Bluetooth (registered trademark), near field communication (NFC), or a wireless USB (WUSB). Furthermore, the in-vehicle device I/F 7660 may establish wired connection such as Universal Serial Bus (USB), High-Definition Multimedia Interface (HDMI) (registered trademark), or Mobile High-definition Link (MHL), via connection terminal or cables if necessary (not illustrated). The in-vehicle device 7760 may include, for example, at least one of a mobile device or a wearable device possessed by an occupant, or an information device loaded or mounted on the vehicle. Further, the in-vehicle device 7760 may include a navigation device that searches and offers a route to a certain destination. The in-vehicle device I/F 7660 exchanges control signals or data signals with these in-vehicle devices 7760.

The in-vehicle network I/F 7680 is an interface mediating communication between the microcomputer 7610 and the communication network 7010. The in-vehicle network I/F 7680 transmits and receives signals or the like in accordance with a predetermined protocol supported by the communication network 7010.

The microcomputer 7610 of the integrated control unit 7600 controls the vehicle control system 7000 in accordance with various programs on the basis of information obtained via at least one of the general-purpose communication I/F 7620, the dedicated communication I/F 7630, the positioning unit 7640, the beacon receiving unit 7650, the in-vehicle device I/F 7660, or the in-vehicle network I/F 7680. For example, the microcomputer 7610 may calculate a control target value of the driving force generation apparatus, the steering mechanism, or the braking apparatus on the basis of the obtained vehicle external/internal information and may output a control command to the drive system control unit 7100. For example, the microcomputer 7610 may perform cooperative control for the purpose of achieving a function of an advanced driver assistance system (ADAS) including collision avoidance or impact mitigation of vehicles, follow-up running based on inter-vehicle distance, cruise control, vehicle collision warning, vehicle lane departure warning, and the like. Furthermore, it is allowable such that the microcomputer 7610 controls the driving force generation apparatus, the steering mechanism, the braking apparatus, or the like, on the basis of the obtained information regarding the surroundings of the vehicle, thereby performing cooperative control for the purpose of automatic driving of performing autonomous traveling without depending on the operation of the driver, for example.

The microcomputer 7610 may generate three-dimensional distance information between a vehicle and an object such as surrounding structure and a person and may create local map information including peripheral information of the vehicle current position on the basis of information obtained via at least one of the general-purpose communication I/F 7620, the dedicated communication I/F 7630, the positioning unit 7640, the beacon receiving unit 7650, the in-vehicle device I/F 7660, or the in-vehicle network I/F 7680. Furthermore, on the basis of the obtained information, the microcomputer 7610 may predict danger such as vehicle collision, presence of a pedestrian, etc. in the vicinity, or entrance into a road closed to traffic and then may generate a warning signal. The warning signal may be, for example, a signal for generating an alarm sound or for turning on a warning lamp.

The audio image output unit 7670 transmits an output signal in the form of at least one of audio or image to an output apparatus capable of visually or audibly notifying the occupant of the vehicle or the outside of the vehicle of information. In the example of FIG. 12, an audio speaker 7710, a display unit 7720, and an instrument panel 7730 are illustrated as exemplary output apparatuses. The display unit 7720 may include at least one of an on-board display or a head-up display, for example. The display unit 7720 may have an augmented reality (AR) display function. The output apparatus may be a wearable device such as a headphone, an eyeglass type display worn by an occupant, a projector, a lamp, or the like other than these devices. In a case where the output apparatus is a display apparatus, the display apparatus visually displays results obtained by various processing performed by the microcomputer 7610 or information received from other control units in various formats such as text, image, table, or graph. Furthermore, in a case where the output apparatus is an audio output apparatus, the audio output apparatus audibly outputs an analog signal obtained by conversion of an audio signal constituted with the reproduced audio data, acoustic data, or the like.

Note that in the example illustrated in FIG. 12, at least two control units connected via the communication network 7010 may be integrated as one control unit. Alternatively, each of the control units may be constituted with a plurality of control units. In addition, the vehicle control system 7000 may include another control unit that is not illustrated. Furthermore, in the above description, some or all of the functions executed by any one of the control units may be provided by the other control unit. That is, as long as information is transmitted and received via the communication network 7010, predetermined arithmetic processing may be performed by any of the control units. Similarly, a sensor or a device connected to any control unit may be connected to another control unit, and a plurality of control units may exchange detection information with each other via the communication network 7010.

The technology according to the present disclosure can be suitably applied to the imaging unit 7410 connected to the vehicle exterior information detection unit 7400 out of the above-described configuration. Specifically, the camera module according to the above-described first embodiment and the second embodiment can be used as the imaging units 7910, 7912, 7914, 7916, and 7918 provided on the nose, the side mirror, the rear bumper, the back door, the upper part of the windshield in the passenger compartment, or the like, of the vehicle 7900. Application of the technology according to the present disclosure to the imaging units 7910, 7912, 7914, 7916, and 7918 would reduce the number of lenses in the optical system, and this would lead to reduction of the cost of the imaging units 7910, 7912, 7914, 7916, and 7918. Furthermore, since the problem of the small aperture diffraction of the lens of the optical system can be solved by the technology according to the present disclosure, it is possible to increase the number of pixels of the imaging element, and as a result, a clearer image can be obtained.

<Configuration Achievable by the Present Disclosure>

Note that the present disclosure can also be configured as follows.

[A01] <<Imaging Optical System>>
An imaging optical system including:
a lens; and an optical member,
in which the optical member is configured such that a light transmittance value at least in a peripheral portion is larger than a light transmittance value in a central portion.

[A02] The imaging optical system according to [A01],
in which the optical member is formed with an ND filter in which the light transmittance increases from its central portion to its peripheral portion.

[A03] The imaging optical system according to [A01] or [A02],
in which the light transmittance of the optical member is adapted to a light amount characteristic of the lens.

[A04] The imaging optical system according to any one of [A01] to [A03],
in which the optical member is disposed to be separated from the lens or is formed on the lens.

[A05] the imaging optical system according to any one of [A01] to [A04],
in which the optical member is disposed to be separated from an infrared cut filter or is formed on the infrared cut filter.

[B01] <<Camera Module>>
A camera module including the imaging optical system according to any one of [A01] to [A05].

[B02] The camera module according to [B01], including a solid-state imaging element accommodated in a package including a light-transmissive material and configured to receive light that has passed through the imaging optical system.

[C01] <<Camera Module>>
An imaging optical system including:
a lens; and an optical member,
in which the optical member is configured such that a light transmittance value at least in a peripheral portion is larger than a light transmittance value in a central portion.

[C02] The camera module according to [C01], including a solid-state imaging element accommodated in a package including a light-transmissive material and configured to receive light that has passed through the imaging optical system.

[C03] The camera module according to [C01] or [C02],
in which the optical member is formed with an ND filter in which the light transmittance increases from its central portion to its peripheral portion.

[C04] The camera module according to any one of [C01] to [C03],
in which the light transmittance of the optical member is adapted to a light amount characteristic of the lens.

[C05] The camera module according to any one of [C01] to [C04],
in which the optical member is disposed to be separated from the lens or is formed on the lens.

[C06] The camera module according to any one of [C01] to [C05],
in which the optical member is disposed to be separated from an infrared cut filter or is formed on the infrared cut filter.

[D01] <<Electronic Device>>
An electronic device including a solid-state imaging element and the imaging optical system according to any one of [A01] to [A05].

[E01] <<Electronic Device>>
An imaging optical system including a solid-state imaging element; and an imaging optical system including a lens and an optical member,
in which the optical member is configured such that a light transmittance value at least in a peripheral portion is larger than a light transmittance value in a central portion.

[E02] The electronic device according to [E01],
in which the solid-state imaging element is accommodated in a package including a light-transmissive material and configured to receive light that has passed through the imaging optical system.

[E03] The electronic device according to [E01] or [E02],
in which the optical member is formed with an ND filter in which the light transmittance increases from its central portion to its peripheral portion.

[E04] The electronic device according to any one of [E01] to [E03],
in which the light transmittance of the optical member is adapted to a light amount characteristic of the lens.

[E05] The electronic device according to any one of [E01] to [E04],
in which the optical member is disposed to be separated from the lens or is formed on the lens.

[E06] The electronic device according to any one of [E01] to [E05], including an infrared cut filter,
in which the optical member is disposed to be separated from the infrared cut filter or is formed on the infrared cut filter.

REFERENCE SIGNS LIST

10 Camera module
11 Condenser lens
12 Lens driving unit
13 IR Cut Filter (infrared cut filter)
14 ND filter (gradation ND filter)
15 Solid-state imaging element
16 Circuit substrate
17 Metal wire
18 Package
19 Solder bump

The invention claimed is:

1. An imaging optical system, comprising:
a lens;
a first optical member on a light incident surface of the lens;
a second optical member inside the lens, wherein a first light transmittance value in a peripheral portion of each of the first optical member and the second optical member is larger than a second light transmittance value in a central portion of each of the first optical member and the second optical member; and
an infrared cut filter on a light emitting surface side of the lens.

2. The imaging optical system according to claim 1, wherein
the first optical member includes a Neutral Density (ND) filter, and
a light transmittance value of the first optical member increases from the second light transmittance value of the central portion to the first light transmittance value of the peripheral portion.

3. The imaging optical system according to claim 1, wherein a light transmittance value of the first optical member changes from the first light transmittance value to the second light transmittance value based on a light amount characteristic of the lens.

4. A camera module, comprising:
an imaging optical system that includes:
a lens;
a first optical member on a light incident surface of the lens;
a second optical member inside the lens, wherein a first light transmittance value in a peripheral portion of each of the first optical member and the second optical member is larger than a second light transmittance value in a central portion of each of the first optical member and the second optical member; and
an infrared cut filter on a light emitting surface side of the lens.

5. The camera module according to claim 4, further comprising:
a package that includes a light-transmissive material; and
a solid-state imaging element in the package, wherein the solid-state imaging element is configured to receive light through the imaging optical system.

6. An electronic device, comprising:
a solid-state imaging element; and
an imaging optical system that includes:
a lens;
a first optical member on a light incident surface of the lens;
a second optical member inside the lens, wherein a first light transmittance value in a peripheral portion of each of the first optical member and the second optical member is larger than a second light transmittance value in a central portion of each of the first optical member and the second optical member; and
an infrared cut filter on a light emitting surface side of the lens.

* * * * *